United States Patent
Manwaring et al.

(10) Patent No.: US 9,107,666 B2
(45) Date of Patent: *Aug. 18, 2015

(54) THERMAL RESECTING LOOP

(75) Inventors: Kim Manwaring, Phoenix, AZ (US); David McNally, Salt Lake City, UT (US)

(73) Assignee: Domain Surgical, Inc., Salt Lake City, UT (US)

( * ) Notice: Subject to any disclaimer, the term of this patent is extended or adjusted under 35 U.S.C. 154(b) by 357 days.

This patent is subject to a terminal disclaimer.

(21) Appl. No.: 13/545,922

(22) Filed: Jul. 10, 2012

(65) Prior Publication Data

US 2012/0330295 A1   Dec. 27, 2012

Related U.S. Application Data

(63) Continuation-in-part of application No. 12/647,340, filed on Dec. 24, 2009, now Pat. No. 8,419,724, and a continuation-in-part of application No. 13/441,614, (Continued)

(51) Int. Cl.
*A61B 18/04* (2006.01)
*A61B 18/08* (2006.01)
(Continued)

(52) U.S. Cl.
CPC .............. *A61B 18/082* (2013.01); *A61B 18/10* (2013.01); *A61B 2018/0063* (2013.01);
(Continued)

(58) Field of Classification Search
CPC ............. A61B 1/07; A61B 17/320068; A61B 17/320072; A61B 17/320084; A61B 17/320092; A61B 18/04; A61B 18/18; A61B 2002/2864; A61B 2018/00089; A61B 2018/00095; A61B 2018/00214; A61B 2018/0022; A61B 2018/00601; A61B 2018/00876; A61B 2018/046; A61B 2018/00107; A61F 2002/2864; A61F 2002/4651; A61F 7/123; A61F 9/0079; A61M 2205/368; A61M 2205/3693; A61N 1/40; A61N 1/403; A61N 2/02

USPC .............................. 606/47, 113; 607/98–103
See application file for complete search history.

(56) References Cited

U.S. PATENT DOCUMENTS

| 300,155 A | 6/1884 | Starr |
| 770,368 A | 9/1904 | Heath |

(Continued)

FOREIGN PATENT DOCUMENTS

| EP | 0033958 | 8/1981 |
| EP | 0 130 671 | 9/1985 |

(Continued)

OTHER PUBLICATIONS

Written Opinion of the International Preliminary Examining Authority from related PCT Patent Application No. PCT/US2011/050417, Feb. 6, 2013.

(Continued)

*Primary Examiner* — Jaymi Della
(74) *Attorney, Agent, or Firm* — Snow Christensen & Martineau; Randall B. Bateman; Christopher L. Wight

(57) ABSTRACT

A thermal surgical instrument comprising a conductor having a ferromagnetic material in electrical communication with the conductor, such that passage of electrical energy through the conductor causes substantially uniform heating of the ferromagnetic material sufficient to produce a desired therapeutic tissue effect is provided. The conductor may be shaped to facilitate resection of tissue from a patient and include a support to provide increase rigidity to the loop so that the conductor better resists bending during use. The ferromagnetic material quickly heats and cools in response to a controllable power delivery source. The thermal surgical instrument can be used for substantially simultaneously resecting tissue with hemostasis.

29 Claims, 26 Drawing Sheets

Related U.S. Application Data

(60) filed on Apr. 6, 2012. Provisional application No. 61/170,203, filed on Apr. 17, 2009, provisional application No. 61/170,220, filed on Apr. 17, 2009, provisional application No. 61/170,207, filed on Apr. 17, 2009, provisional application No. 61/473,729, filed on Apr. 8, 2011, provisional application No. 61/506,464, filed on Jul. 11, 2011.

(51) Int. Cl.
*A61B 18/10* (2006.01)
*A61B 18/00* (2006.01)

(52) U.S. Cl.
CPC ............ *A61B 2018/00107* (2013.01); *A61B 2018/00601* (2013.01); *A61B 2018/00625* (2013.01); *A61B 2018/00642* (2013.01); *A61B 2018/00815* (2013.01); *A61B 2018/00821* (2013.01)

(56) References Cited

U.S. PATENT DOCUMENTS

| | | |
|---|---|---|
| 1,104,053 A | 7/1914 | Lea |
| 1,280,052 A | 9/1918 | Lidberg |
| 1,335,987 A | 4/1920 | Reid |
| 1,366,231 A | 1/1921 | Winter et al. |
| 1,401,104 A | 12/1921 | Kruesheld |
| 1,794,296 A | 2/1931 | Hyams |
| 2,027,854 A | 1/1936 | Breth et al. |
| 2,050,904 A | 8/1936 | Trice |
| 2,120,598 A | 6/1938 | Beuoy |
| 2,250,602 A | 7/1941 | Pierce |
| 2,278,633 A | 4/1942 | Bagnall |
| 2,375,154 A | 5/1945 | Volterra |
| 2,412,977 A | 12/1946 | Eskin |
| 2,501,499 A | 3/1950 | Crowley |
| 2,670,425 A | 12/1954 | Stone |
| 2,735,797 A | 2/1956 | Schjeldahl |
| 2,782,290 A | 2/1957 | Lannan et al. |
| 2,831,242 A | 4/1958 | Kieffer et al. |
| 2,846,560 A | 8/1958 | Jacoby et al. |
| 2,863,036 A | 12/1958 | Mitchell et al. |
| 2,947,345 A | 8/1960 | Schjeldahl |
| 2,960,592 A | 11/1960 | Pierce |
| 3,084,242 A | 4/1963 | Vogler et al. |
| 3,213,259 A | 10/1965 | Bennet et al. |
| 3,350,544 A | 10/1967 | Lennox |
| 3,352,011 A | 11/1967 | Alexander et al. |
| 3,400,252 A | 9/1968 | Hayakawa |
| 3,404,202 A | 10/1968 | Carlson et al. |
| 3,413,442 A | 11/1968 | Buiting et al. |
| 3,414,705 A | 12/1968 | Marcoux |
| 3,434,476 A | 3/1969 | Shaw et al. |
| 3,501,619 A | 3/1970 | Buiting et al. |
| 3,515,837 A | 6/1970 | Ando |
| 3,520,043 A | 7/1970 | Darling |
| 3,556,953 A | 1/1971 | Schulz |
| 3,768,482 A | 10/1973 | Shaw |
| 3,825,004 A | 7/1974 | Durden, III |
| 3,826,263 A | 7/1974 | Cage et al. |
| 3,834,392 A | 9/1974 | Lampman et al. |
| 3,978,312 A | 8/1976 | Barton et al. |
| RE29,088 E | 12/1976 | Shaw |
| 4,089,336 A | 5/1978 | Cage et al. |
| 4,091,813 A | 5/1978 | Shaw et al. |
| RE30,190 E | 1/1980 | Shaw |
| 4,185,632 A | 1/1980 | Shaw |
| 4,196,734 A | 4/1980 | Harris |
| 4,198,957 A | 4/1980 | Cage et al. |
| 4,206,759 A | 6/1980 | Shaw |
| 4,207,896 A | 6/1980 | Shaw |
| 4,209,017 A | 6/1980 | Shaw |
| 4,256,945 A | 3/1981 | Carter et al. |
| 4,359,052 A | 11/1982 | Staub |
| 4,364,390 A | 12/1982 | Shaw |
| 4,371,861 A | 2/1983 | Abdelrahman et al. |
| 4,374,517 A | 2/1983 | Hagiwara |
| RE31,723 E | 11/1984 | Shaw |
| 4,481,057 A | 11/1984 | Beard |
| 4,485,810 A | 12/1984 | Beard |
| 4,492,231 A | 1/1985 | Auth |
| 4,493,320 A | 1/1985 | Treat |
| 4,523,084 A | 6/1985 | Tamura et al. |
| 4,549,073 A | 10/1985 | Tamura et al. |
| 4,600,018 A | 7/1986 | James et al. |
| 4,622,966 A | 11/1986 | Beard |
| 4,658,819 A | 4/1987 | Harris et al. |
| 4,658,820 A | 4/1987 | Klicek |
| 4,701,587 A | 10/1987 | Carter et al. |
| 4,752,673 A | 6/1988 | Krumme |
| 4,807,620 A | 2/1989 | Strul |
| 4,839,501 A | 6/1989 | Cowell |
| 4,848,337 A | 7/1989 | Shaw et al. |
| 4,860,745 A | 8/1989 | Farin et al. |
| 4,877,944 A | 10/1989 | Cowell et al. |
| 4,914,267 A | 4/1990 | Derbyshire |
| 4,915,100 A | 4/1990 | Green |
| 4,927,413 A | 5/1990 | Hess |
| 4,938,761 A | 7/1990 | Ensslin |
| 5,003,991 A | 4/1991 | Takayama et al. |
| 5,047,025 A | 9/1991 | Taylor et al. |
| 5,053,595 A | 10/1991 | Derbyshire |
| 5,057,106 A | 10/1991 | Kasevich et al. |
| 5,071,419 A | 12/1991 | Rydell et al. |
| 5,087,256 A | 2/1992 | Taylor et al. |
| 5,087,804 A | 2/1992 | McGaffigan |
| 5,098,429 A | 3/1992 | Sterzer |
| 5,107,095 A | 4/1992 | Derbyshire |
| 5,182,427 A | 1/1993 | McGaffigan |
| 5,189,271 A | 2/1993 | Derbyshire |
| 5,197,649 A | 3/1993 | Bessler et al. |
| 5,203,782 A | 4/1993 | Gudov et al. |
| 5,209,725 A | 5/1993 | Roth |
| 5,211,646 A | 5/1993 | Alperovich et al. |
| 5,217,460 A | 6/1993 | Knoepfler |
| 5,300,068 A | 4/1994 | Rosar et al. |
| 5,300,750 A | 4/1994 | Carter, Jr. et al. |
| 5,308,311 A | 5/1994 | Eggers et al. |
| 5,318,564 A | 6/1994 | Eggers |
| 5,364,392 A | 11/1994 | Warner et al. |
| 5,370,645 A | 12/1994 | Klicek et al. |
| 5,370,675 A | 12/1994 | Edwards et al. |
| 5,376,094 A | 12/1994 | Kline |
| 5,382,247 A | 1/1995 | Cimino et al. |
| 5,400,267 A | 3/1995 | Denen et al. |
| 5,411,508 A | 5/1995 | Bessler et al. |
| 5,423,808 A | 6/1995 | Edwards et al. |
| 5,425,731 A | 6/1995 | Daniel et al. |
| 5,445,635 A | 8/1995 | Denen et al. |
| 5,472,443 A | 12/1995 | Cordis et al. |
| 5,475,203 A | 12/1995 | McGaffigan |
| 5,480,397 A | 1/1996 | Eggers |
| 5,480,398 A | 1/1996 | Eggers |
| 5,496,312 A | 3/1996 | Klicek |
| 5,496,314 A | 3/1996 | Eggers |
| 5,507,743 A | 4/1996 | Edwards et al. |
| 5,540,679 A | 7/1996 | Fram et al. |
| 5,540,681 A | 7/1996 | Strul et al. |
| 5,542,916 A | 8/1996 | Hirsch et al. |
| 5,571,153 A | 11/1996 | Wallsten |
| 5,573,533 A | 11/1996 | Strul |
| 5,593,406 A | 1/1997 | Eggers et al. |
| 5,595,565 A | 1/1997 | Treat et al. |
| 5,611,798 A | 3/1997 | Eggers |
| 5,628,771 A | 5/1997 | Mizukawa et al. |
| 5,674,219 A | 10/1997 | Monson et al. |
| 5,707,369 A | 1/1998 | Vaitekunas et al. |
| 5,707,402 A | 1/1998 | Heim |
| 5,807,392 A | 9/1998 | Eggers |
| 5,807,393 A | 9/1998 | Williamson, IV et al. |
| 5,827,269 A | 10/1998 | Saadat |
| 5,836,874 A | 11/1998 | Swanson et al. |

(56) References Cited

U.S. PATENT DOCUMENTS

| | | | |
|---|---|---|---|
| 5,836,943 | A | 11/1998 | Miller, III |
| 5,843,019 | A * | 12/1998 | Eggers et al. ............ 604/22 |
| 5,911,719 | A | 6/1999 | Eggers |
| 5,964,759 | A | 10/1999 | Yamanashi et al. |
| 6,004,316 | A | 12/1999 | Laufer |
| 6,006,755 | A | 12/1999 | Edwards |
| 6,015,415 | A | 1/2000 | Avellanet |
| 6,035,238 | A | 3/2000 | Ingle et al. |
| 6,038,017 | A | 3/2000 | Pinsukanjana et al. |
| 6,039,733 | A | 3/2000 | Buysse et al. |
| 6,066,138 | A | 5/2000 | Sheffer et al. |
| 6,161,048 | A | 12/2000 | Sluijter et al. |
| 6,190,382 | B1 | 2/2001 | Ormsby et al. |
| 6,210,403 | B1 | 4/2001 | Klicek |
| 6,228,084 | B1 | 5/2001 | Kirwan, Jr. |
| 6,241,723 | B1 | 6/2001 | Heim et al. |
| 6,287,305 | B1 | 9/2001 | Heim et al. |
| 6,290,697 | B1 | 9/2001 | Tu et al. |
| 6,350,262 | B1 | 2/2002 | Ashley |
| 6,358,273 | B1 | 3/2002 | Strul et al. |
| 6,454,781 | B1 | 9/2002 | Witt et al. |
| 6,533,781 | B2 | 3/2003 | Heim et al. |
| 6,602,252 | B2 | 8/2003 | Mollenauer |
| 6,604,003 | B2 | 8/2003 | Fredricks et al. |
| 6,626,901 | B1 | 9/2003 | Treat et al. |
| 6,632,182 | B1 | 10/2003 | Treat |
| 6,692,489 | B1 | 2/2004 | Heim et al. |
| 6,726,683 | B1 | 4/2004 | Shaw |
| 6,821,273 | B2 | 11/2004 | Mollenauer |
| 6,860,880 | B2 | 3/2005 | Treat et al. |
| 6,908,463 | B2 | 6/2005 | Treat et al. |
| 6,911,026 | B1 | 6/2005 | Hall et al. |
| 6,912,911 | B2 | 7/2005 | Oh et al. |
| 6,980,862 | B2 | 12/2005 | Fredricks et al. |
| 6,980,865 | B1 | 12/2005 | Wang et al. |
| 7,011,656 | B2 | 3/2006 | McGaffigan |
| 7,025,065 | B2 | 4/2006 | McGaffigan et al. |
| 7,083,613 | B2 | 8/2006 | Treat |
| 7,112,201 | B2 | 9/2006 | Truckai et al. |
| 7,122,030 | B2 | 10/2006 | Flores et al. |
| 7,164,968 | B2 | 1/2007 | Treat et al. |
| 7,175,621 | B2 | 2/2007 | Heim et al. |
| 7,211,079 | B2 | 5/2007 | Treat |
| 7,211,080 | B2 | 5/2007 | Treat et al. |
| 7,235,073 | B2 | 6/2007 | Levine et al. |
| 7,300,452 | B2 | 11/2007 | Gleich |
| 7,317,275 | B2 | 1/2008 | Treat |
| 7,326,202 | B2 | 2/2008 | McGaffigan |
| 7,329,255 | B2 | 2/2008 | McGaffigan |
| 7,377,919 | B2 | 5/2008 | Heim et al. |
| 7,396,356 | B2 | 7/2008 | Mollenauer |
| 7,435,249 | B2 | 10/2008 | Buysse et al. |
| 7,473,250 | B2 | 1/2009 | Makin et al. |
| 7,473,253 | B2 | 1/2009 | Dycus et al. |
| 7,494,492 | B2 | 2/2009 | Da Silva et al. |
| 7,528,663 | B2 | 5/2009 | Naletov et al. |
| 7,533,719 | B2 | 5/2009 | Hinson |
| 7,540,324 | B2 | 6/2009 | de Rouffignac |
| 7,549,470 | B2 | 6/2009 | Vinegar |
| 7,553,309 | B2 | 6/2009 | Buysse et al. |
| 7,556,095 | B2 | 7/2009 | Vinegar |
| 7,556,096 | B2 | 7/2009 | Vinegar |
| 7,559,367 | B2 | 7/2009 | Vinegar |
| 7,559,368 | B2 | 7/2009 | Vinegar |
| 7,562,706 | B2 | 7/2009 | Li et al. |
| 7,562,707 | B2 | 7/2009 | Miller |
| 7,578,815 | B2 | 8/2009 | Howell |
| 7,581,589 | B2 | 9/2009 | Roes et al. |
| 7,584,789 | B2 | 9/2009 | Mo et al. |
| 7,588,565 | B2 | 9/2009 | Marchitto et al. |
| 7,588,566 | B2 | 9/2009 | Treat et al. |
| 7,591,310 | B2 | 9/2009 | Minderhoud |
| 7,597,147 | B2 | 10/2009 | Vitek |
| 7,604,052 | B2 | 10/2009 | Roes |
| 7,610,962 | B2 | 11/2009 | Fowler |
| 7,613,523 | B2 | 11/2009 | Eggers et al. |
| 7,631,689 | B2 | 12/2009 | Vinegar |
| 7,631,690 | B2 | 12/2009 | Vinegar |
| 7,632,295 | B2 | 12/2009 | Flores |
| 7,635,023 | B2 | 12/2009 | Goldberg |
| 7,635,024 | B2 | 12/2009 | Karanikas |
| 7,635,025 | B2 | 12/2009 | Vinegar |
| 7,678,105 | B2 | 3/2010 | McGreevy et al. |
| 7,686,804 | B2 | 3/2010 | Johnson et al. |
| 7,699,842 | B2 | 4/2010 | Buysse et al. |
| 7,702,397 | B2 | 4/2010 | Fredricks et al. |
| 7,776,035 | B2 | 8/2010 | Rick et al. |
| 7,828,798 | B2 | 11/2010 | Buysse et al. |
| 7,871,406 | B2 | 1/2011 | Nields et al. |
| 7,879,033 | B2 | 2/2011 | Sartor et al. |
| 7,887,535 | B2 | 2/2011 | Lands et al. |
| 7,922,713 | B2 | 4/2011 | Geisel |
| 7,931,649 | B2 | 4/2011 | Couture et al. |
| 7,938,779 | B2 | 5/2011 | Sakurai et al. |
| 7,951,149 | B2 | 5/2011 | Carlton |
| 7,951,150 | B2 | 5/2011 | Johnson et al. |
| 7,959,633 | B2 | 6/2011 | Sartor et al. |
| 7,963,965 | B2 | 6/2011 | Buysse et al. |
| 7,972,334 | B2 | 7/2011 | Mcgreevy et al. |
| 7,972,335 | B2 | 7/2011 | Mcgreevy et al. |
| 7,981,113 | B2 | 7/2011 | Truckai et al. |
| 8,062,290 | B2 | 11/2011 | Buysse et al. |
| 8,100,896 | B2 | 1/2012 | Rodhajsky |
| 8,100,908 | B2 | 1/2012 | Mcgaffigan et al. |
| 8,104,956 | B2 | 1/2012 | Blaha |
| 8,105,323 | B2 | 1/2012 | Buysse et al. |
| 8,211,105 | B2 | 7/2012 | Buysse et al. |
| 8,241,284 | B2 | 8/2012 | Dycus et al. |
| 8,287,528 | B2 | 10/2012 | Wham et al. |
| 8,377,052 | B2 | 2/2013 | Marwaring et al. |
| 8,377,057 | B2 | 2/2013 | Rick et al. |
| 8,398,626 | B2 | 3/2013 | Buysse et al. |
| 8,480,666 | B2 | 7/2013 | Buysse et al. |
| 8,568,402 | B2 | 10/2013 | Buysse et al. |
| 8,591,506 | B2 | 11/2013 | Wham et al. |
| 8,667,674 | B2 | 3/2014 | Buysse |
| 8,672,938 | B2 | 3/2014 | Buysse et al. |
| 2001/0014804 | A1 | 8/2001 | Goble et al. |
| 2002/0019627 | A1 | 2/2002 | Maguire et al. |
| 2002/0019644 | A1 | 2/2002 | Hastings et al. |
| 2002/0026188 | A1 | 2/2002 | Balbierz et al. |
| 2002/0029037 | A1 | 3/2002 | Kim |
| 2002/0029062 | A1 | 3/2002 | Satake |
| 2002/0068931 | A1 | 6/2002 | Wong et al. |
| 2002/0087156 | A1 | 7/2002 | Maguire et al. |
| 2002/0120261 | A1 | 8/2002 | Balbierz et al. |
| 2002/0133148 | A1 | 9/2002 | Daniel et al. |
| 2002/0173787 | A1 | 11/2002 | Buysse et al. |
| 2003/0004507 | A1 | 1/2003 | Francischelli et al. |
| 2003/0055417 | A1 | 3/2003 | Truckai et al. |
| 2003/0055424 | A1 | 3/2003 | Ciarrocca |
| 2003/0060818 | A1 | 3/2003 | Kannenberg et al. |
| 2003/0073987 | A1 | 4/2003 | Sakurai et al. |
| 2003/0073989 | A1 | 4/2003 | Hoey et al. |
| 2003/0109871 | A1 | 6/2003 | Johnson et al. |
| 2003/0144660 | A1 | 7/2003 | Mollenauer |
| 2003/0171747 | A1 | 9/2003 | Kanehira et al. |
| 2003/0176873 | A1 | 9/2003 | Chernenko et al. |
| 2003/0195499 | A1 | 10/2003 | Prakash et al. |
| 2003/0199755 | A1 | 10/2003 | Halperin |
| 2004/0006335 | A1 | 1/2004 | Garrison |
| 2004/0030330 | A1 | 2/2004 | Brassell et al. |
| 2004/0034349 | A1 | 2/2004 | Kirwan, Jr. et al. |
| 2004/0049185 | A1 | 3/2004 | Latterell et al. |
| 2004/0059345 | A1 | 3/2004 | Nakao et al. |
| 2004/0073256 | A1 | 4/2004 | Marchitto |
| 2004/0167506 | A1 | 8/2004 | Chen |
| 2004/0176756 | A1 | 9/2004 | McGaffigan |
| 2004/0187875 | A1 | 9/2004 | He et al. |
| 2004/0243120 | A1 | 12/2004 | Orszulak et al. |
| 2005/0021016 | A1 | 1/2005 | Malecki et al. |
| 2005/0033338 | A1 | 2/2005 | Ferree |
| 2005/0072827 | A1 | 4/2005 | Mollenauer |
| 2005/0107776 | A1 | 5/2005 | Mcgaffigan et al. |

(56) References Cited

U.S. PATENT DOCUMENTS

| | | |
|---|---|---|
| 2005/0113824 A1 | 5/2005 | Sartor et al. |
| 2005/0197661 A1 | 9/2005 | Carrison et al. |
| 2005/0245919 A1 | 11/2005 | Van der Welde |
| 2005/0273111 A1 | 12/2005 | Ferree et al. |
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0127706 A1 | 6/2006 | Goebel et al. |
| 2006/0142824 A1 | 6/2006 | Zikorus et al. |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217700 A1 | 9/2006 | Garito et al. |
| 2006/0217706 A1 | 9/2006 | Lau et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0016181 A1 | 1/2007 | van der Weide et al. |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0106294 A1 | 5/2007 | Nesbitt |
| 2007/0127897 A1 | 6/2007 | John et al. |
| 2007/0131428 A1 | 6/2007 | Willem Cornelis den Boestert et al. |
| 2007/0173811 A1 | 7/2007 | Couture et al. |
| 2007/0208339 A1 | 9/2007 | Arts et al. |
| 2007/0239151 A1 | 10/2007 | Atalar et al. |
| 2007/0270924 A1 | 11/2007 | McCann et al. |
| 2008/0017380 A1 | 1/2008 | Vinegar |
| 2008/0033419 A1 | 2/2008 | Nields et al. |
| 2008/0035346 A1 | 2/2008 | Nair et al. |
| 2008/0035347 A1 | 2/2008 | Brady |
| 2008/0035705 A1 | 2/2008 | Menotti |
| 2008/0038144 A1 | 2/2008 | Maziasz |
| 2008/0077129 A1 | 3/2008 | Van Wyk et al. |
| 2008/0119841 A1 | 5/2008 | Geisel |
| 2008/0128134 A1 | 6/2008 | Mudunuri et al. |
| 2008/0135253 A1 | 6/2008 | Vinegar |
| 2008/0135254 A1 | 6/2008 | Vinegar |
| 2008/0142216 A1 | 6/2008 | Vinegar |
| 2008/0142217 A1 | 6/2008 | Pieterson |
| 2008/0161800 A1 | 7/2008 | Wang et al. |
| 2008/0173444 A1 | 7/2008 | Stone et al. |
| 2008/0174115 A1 | 7/2008 | Lambirth |
| 2008/0185147 A1 | 8/2008 | Vinegar |
| 2008/0187989 A1 | 8/2008 | McGreevy et al. |
| 2008/0217003 A1 | 9/2008 | Kuhlman |
| 2008/0217016 A1 | 9/2008 | Stegemeier |
| 2008/0228135 A1 | 9/2008 | Snoderly |
| 2008/0236831 A1 | 10/2008 | Hsu |
| 2008/0277113 A1 | 11/2008 | Stegemeier |
| 2008/0281310 A1 | 11/2008 | Dunning et al. |
| 2008/0281315 A1 | 11/2008 | Gines |
| 2008/0319438 A1 | 12/2008 | DeCarlo |
| 2009/0014180 A1 | 1/2009 | Stegemeier |
| 2009/0014181 A1 | 1/2009 | Vinegar |
| 2009/0093811 A1 | 4/2009 | Koblish et al. |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | McGaffigan |
| 2009/0248002 A1 | 10/2009 | Takashino et al. |
| 2009/0292347 A1 | 11/2009 | Asmus et al. |
| 2009/0306644 A1 | 12/2009 | Mayse et al. |
| 2009/0312753 A1 | 12/2009 | Shadduck |
| 2010/0004650 A1 | 1/2010 | Ormsby et al. |
| 2010/0082022 A1 | 4/2010 | Haley et al. |
| 2010/0152725 A1 | 6/2010 | Pearson et al. |
| 2010/0198216 A1 | 8/2010 | Palanker |
| 2010/0228244 A1 | 9/2010 | Hancock et al. |
| 2010/0268218 A1 | 10/2010 | Ormsby et al. |
| 2011/0004204 A1 | 1/2011 | Dodde et al. |
| 2011/0054456 A1 | 3/2011 | Thompson et al. |
| 2011/0092971 A1 | 4/2011 | Sartor et al. |
| 2011/0152857 A1 | 6/2011 | Ingle |
| 2012/0059367 A1 | 3/2012 | Buysse et al. |
| 2012/0130256 A1 | 5/2012 | Buysse et al. |
| 2012/0150170 A1 | 6/2012 | Buysse et al. |
| 2012/0303026 A1 | 11/2012 | Dycus et al. |
| 2013/0041367 A1 | 2/2013 | Wham et al. |
| 2014/0058381 A1 | 2/2014 | Wham et al. |
| 2014/0058384 A1 | 2/2014 | Buysse et al. |
| 2014/0058385 A1 | 2/2014 | Wham et al. |
| 2014/0100559 A1 | 4/2014 | Wham et al. |
| 2014/0180266 A1 | 6/2014 | Buysse et al. |

FOREIGN PATENT DOCUMENTS

| | | |
|---|---|---|
| EP | 2036512 A1 | 3/2009 |
| EP | 2070486 | 6/2009 |
| GB | 2 022 974 | 12/1978 |
| GB | 1 546 624 | 5/1979 |
| JP | 03-051179 | 6/1987 |
| JP | 2558584 | 9/1996 |
| RU | 2 072 118 | 1/1997 |
| WO | WO-82/00746 | 3/1982 |
| WO | WO 92/17121 | 10/1992 |
| WO | WO-93/21839 | 11/1993 |
| WO | WO-96/26677 | 11/1996 |
| WO | WO 9937227 A1 | 7/1999 |
| WO | WO-01/06943 | 2/2001 |
| WO | WO-2004/014217 | 2/2004 |
| WO | WO-2004/076146 | 9/2004 |
| WO | WO-2006/017517 | 2/2006 |
| WO | WO-2006/029649 | 3/2006 |
| WO | WO 2007080578 A2 | 7/2007 |
| WO | WO-2008/060668 | 5/2008 |

OTHER PUBLICATIONS

Visioli, Antonio. Practice PID Control: London: Springer-Verlag, 2006. 1-18. Print.
Center for Research in Scientific Computation. *A Domain Wall Theory for Ferroelectric Hysteresis*, Jan. 1999.
International Preliminary Report on Patentability from related PCT Patent Application No. PCT/US2010/031114, Nov. 1, 2011.
International Search Report from related PCT Patent Application No. PCT/US2010/031114, Jan. 21, 2011.
Metcal Soldering Iron Catalog—2006.
URSI EMTS 2004, pp. 489-491, *Electromagnetic Probes for Living Tissue Cauterization*.
"High Temp Metals." NI2001201 Technical Data. High Temp Metals, Inc., n.d. Web. Jul. 13, 2012. <http://www.hightempmetals.com/techdatafnitempNi200data.php.
International Search Report and Written Opinion from related PCT Application US2012/032659, Oct. 8, 2013.
International Search Report and Written Opinion from related PCT Application US2012/032565, Oct. 8, 2013.
International Preliminary Report on Patentability from PCT/US2012/068027, dated Jun. 10, 2014.
International Search Report and Written Opinion from related PCT Application US2012/038005, Nov. 19, 2013.
International Preliminary Report on Patentability from related PCT Patent Application No. PCT/US2012/032659, Nov. 23, 2012.
International Preliminary Report on Patentability from related PCT Patent Application No. PCT/US2012/038005, Nov. 23, 2012.
International Preliminary Report on Patentability from related PCT Patent Application No. PCT/US2012/032656, Oct. 23, 2012.
Translation of Office Action from related Japanese Patent Application No. 2012-506188, PCT US2010-031114.

(56) References Cited

OTHER PUBLICATIONS

International Search Report and Written Opinion from related PCT Application US2012/032661, Aug. 19, 2013.
International Preliminary Report on Patentability from related PCT Patent Application No. PCT/US2011/050417, Apr. 12, 2012.
International Preliminary Report on Patentability from related PCT Patent Application No. PCT/US2012/055229, Feb. 1, 2013.
International Preliminary Report on Patentability from related PCT Patent Application No. PCT/US2012/068027, Feb. 25, 2013.
European Search Report from European Application No. 12865504.0-1652, dated Nov. 28, 2014.

* cited by examiner

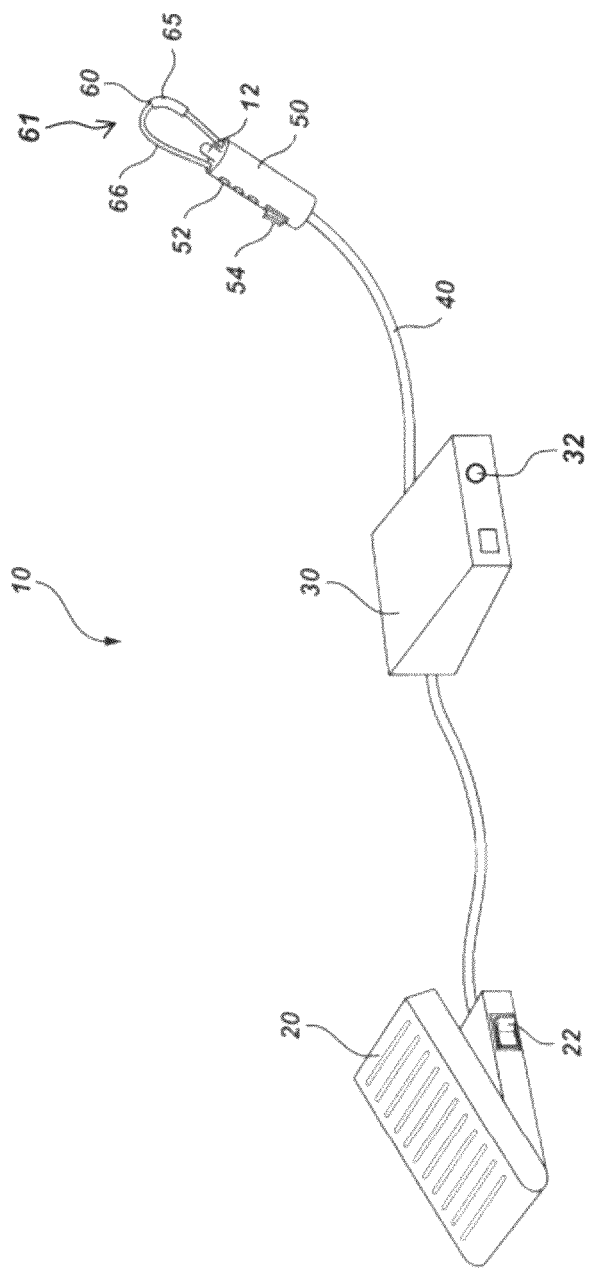

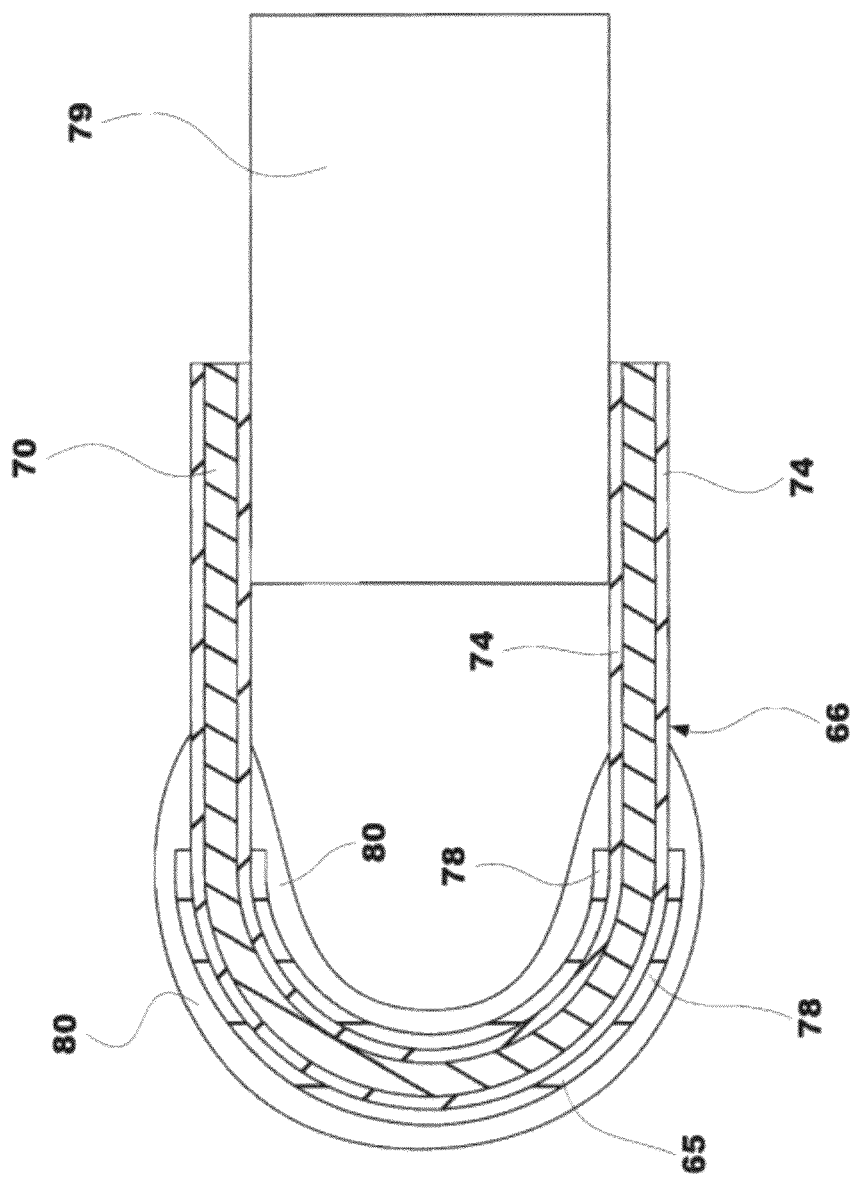

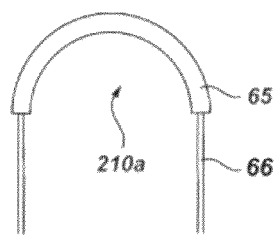 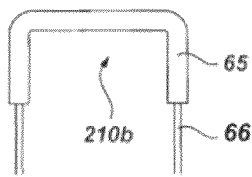 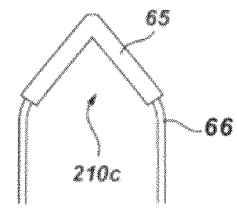
*Fig. 7A*    *Fig. 7B*    *Fig. 7C*
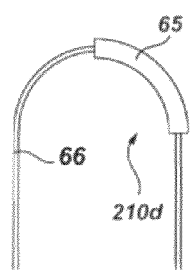 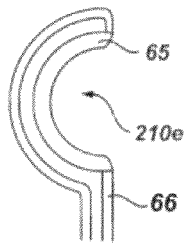 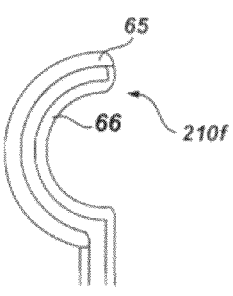 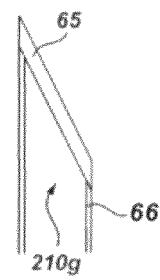
*Fig. 7D*　*Fig. 7E*　*Fig. 7F*　*Fig. 7G*

THERMAL RESECTING LOOP

RELATED APPLICATIONS

The present application is a continuation-in-part of U.S. patent application Ser. No. 12/647,340, filed Dec. 24, 2009 now U.S. Pat. No. 8,419,724, which claims the benefit of U.S. Provisional Patent Application Ser. No. 61/170,203, filed Apr. 17, 2009, U.S. Provisional Patent Application Ser. No. 61/170,220, filed Apr. 17, 2009, and U.S. Provisional Patent Application Ser. No. 61/170,207, filed Apr. 17, 2009, which are incorporated hereby by references in their entirety. The present application is also a continuation-in-part of U.S. patent application Ser. No. 13/441,614, filed Apr. 6, 2012, which claims the benefit of U.S. Provisional Patent Application Ser. No. 61/473,729, filed Apr. 8, 2011, which are incorporated hereby by references in their entirety. The present application also claims the benefit of U.S. Provisional Application Ser. No. 61/506,464, filed on Jul. 11, 2011, which is incorporated herein by reference in its entirety.

BACKGROUND OF THE INVENTION

1. The Field of the Invention

The present invention relates to surgical instruments. More specifically, the present invention relates to thermally adjustable resecting loops used in open and minimally invasive surgical procedures and interventional surgical and therapeutic procedures.

2. State of the Art

Surgery generally involves cutting, repairing and/or removing tissue or other materials. These applications are generally performed by cutting tissue, fusing tissue, or tissue destruction.

Current electrosurgery modalities used for cutting, coagulating, desiccating, ablating, or fulgurating tissue, have undesirable side effects and drawbacks. For example, monopolar and bipolar electrosurgery modalities generally have disadvantages relating to "beyond the tip" effects. These effects are caused by intentionally passing alternating current through tissues in contact with conducting instruments or probes.

Monopolar surgical instruments require electric current to pass through the patient. A return electrode is placed on the patient, often on the patient's thigh. Electricity is conducted from a "knife" or "loop" electrode through the tissue and returns through the return electrode. Other forms of monopolar instruments exist, such as those which use the capacitive effect of the body to act as the return electrode or ground.

A low voltage high frequency waveform will incise, but has little hemostatic effect. A high voltage waveform will cause adjacent tissue hemostasis and coagulation. Therefore, when hemostasis is desirable, high voltage is used. The high voltage spark frequently has deeper tissue effects than the cut because the electricity must pass through the patient. The damage to the tissue extends away from the actual point of coagulation. Furthermore, there are complaints of return electrode burns. Yet, any reduction of voltage reduces the effectiveness of hemostasis. Further, the temperature of the spark or arc cannot be precisely controlled, which can lead to undesirable charring of target tissue.

Bipolar surgical instruments can produce tissue damage and problems similar to monopolar devices, such as sparking, charring, deeper tissue effects and electric current damage away from the application of energy with varying effects due to the difference in electrical conductivity of tissue types, such as nerve, muscle, fat and bone, and into adjacent tissues of the patient. However, the current is more, but not completely, contained between the bipolar electrodes. These electrodes are also generally more expensive because there are at least two precision electrodes that must be fabricated instead of the one monopolar electrode.

Electrocautery resistive heating elements reduce the drawbacks associated with charring and deeper tissue damage caused by other electrosurgery methods. However, such devices often present other tradeoffs, such as the latency in controlling heating and cooling time, and effective power delivery. Many resistive heating elements have slow heating and cooling times, which makes it difficult for the surgeon to work through or around tissue without causing incidental damage. Additionally, tissue destruction with resistively heated tools can produce unintended collateral tissue damage.

Tissue destruction instruments generally heat tissue to a predetermined temperature for a period of time to kill or ablate the tissue. In some controlled heating of tissues, a laser is directed to an absorptive cap to reach and maintain a predetermined temperature for a predetermined amount of time. While this provides the benefits of thermal heating, it is expensive due to the complexity and expense of laser hardware.

In another tissue destruction procedure, a microwave antenna array is inserted into the tissue. These arrays are powered by instruments that cause microwave energy to enter and heat the tissue. While such devices are often effective at killing or ablating the desired tissue, they often cause deeper tissue effects than the desired area. Additionally the procedures can require expensive equipment.

Uses of ferrite beads and alloy mixes in ceramics have been examined as an alternative to other tissue destruction methods. When excited by the magnetic field associated with high frequency current passing through a conductor, ferrite beads and alloy mixes in ceramics can reach high temperatures very quickly. However, one major problem with the use of these materials is that a large temperature differential can cause the material to fracture, especially when it comes into and out of contact with liquids. In other words, if a hot ferrite surgical instrument is quenched by a cooler pool of liquid, such as blood or other body fluids, the material's corresponding temperature drops rapidly and may cause the material to fracture. These fractures not only cause the tool to lose its effectiveness as a heat source, because the magnetic field is disrupted, but may require extraction of the material from the patient. Obviously, the need to extract small pieces of ferrite product from a patient is highly undesirable.

In addition, removing tissue can be complicated. Removal of tissue with a blade may require several incisions or a delicate hand with complicated movements. Furthermore, access to a tumor may be from an angle perpendicular to the tissue. There may be little room to maneuver a blade and its handpiece to the side. This can make resecting a piece of tissue more difficult than simply cutting through tissue. Alternatively, lasers or bipolar forceps can be employed to produce heat to dessicate the surface of the target tissue, which can then be removed with forceps, and then the heat applied again in order to remove the next layer of tissue if necessary. This process can be tedious and produce unwanted bleeding that may obscure vision, complicate the surgery and jeopardize the well-being of the patient.

Thus, there is a need for an improved thermal surgical tool to remove tissue.

SUMMARY OF THE INVENTION

It is an object of the present invention to provide an improved thermally adjustable surgical or therapeutic tool.

According to one aspect of the invention, a thermal surgical instrument system is provided with an arc-shaped, looped or rounded conductor having one or more ferromagnetic layers disposed along a length of the conductor, and an oscillating electrical energy source for generating uniform ferromagnetic heating at the location of the one or more ferromagnetic layers with a small heat latency. This may provide the advantage of allowing the surgeon to resect tissue, such as tumors or tissue around tumors, while reducing or eliminating bleeding. The instrument may seal along the coated section of the loop as it cuts through the tissue. Thus, a surgeon may scoop out portions of tissue with a hemostatic effect reducing or eliminating bleeding from the remaining tissue. The scooping motion may be made with the handpiece generally perpendicular to the tissue, thus enabling easier removal of tissue. Further, the same loop can be turned ninety degrees and be used to cut like a knife, with the same hemostatic effect.

According to another aspect of the invention, a thermal surgical instrument may include a support to provide increase rigidity to the loop so that it better resists bending during use. The support may include at least one conductive intervening layer thereon with a ferromagnetic material disposed in communication with the at least one conductive intervening layer.

According to another aspect of the invention, the support may be selected from a material with desired rigidity/flexibility characteristics for the particular procedure being performed and may be conductive or non-conductive.

According to another aspect of the invention, a thermal surgical instrument may include a body, such as a handpiece, and a cutting element disposed at an angle such that the cutting element is oriented in a non-parallel position with respect to the handpiece. The angle of the cutting element may allow better access to tissue within confined spaces. It may also provide a better view of the surgical site because the cutting element is off of the center axis of the handpiece These and other aspects of the present invention are realized in a thermally adjustable instrument as shown and described in the following figures and related description.

BRIEF DESCRIPTION OF THE DRAWINGS

Various embodiments of the present invention are shown and described in reference to the numbered drawings wherein:

FIG. 1 shows a perspective view of a thermal surgical instrument system in accordance with the principles of the present invention;

FIG. 4C shows a side cross-sectional view of a portion of a thermal surgical tool system according to principles of the present invention;

FIG. 7A shows a close-up view of ferromagnetic conductor surgical instrument tip with a loop geometry in accordance with one aspect of the present invention;

FIG. 7B shows a close-up view of a ferromagnetic conductor surgical instrument tip with a generally square geometry in accordance with one aspect of the present invention;

FIG. 7C shows a close-up view of a ferromagnetic conductor surgical instrument tip with a pointed geometry;

FIG. 7D shows a close-up view of a ferromagnetic conductor surgical instrument tip with an asymmetrical loop geometry;

FIG. 7E shows a close-up view of a ferromagnetic conductor surgical instrument tip with a hook geometry in which the concave portion may be used for therapeutic effect, including cutting;

FIG. 7F shows a close up view of a ferromagnetic conductor surgical instrument tip with a hook geometry in which the convex portion may be used for therapeutic effect, including cutting;

FIG. 7G shows a close up view of a ferromagnetic conductor surgical instrument tip with an angled geometry;

Figure 1A:
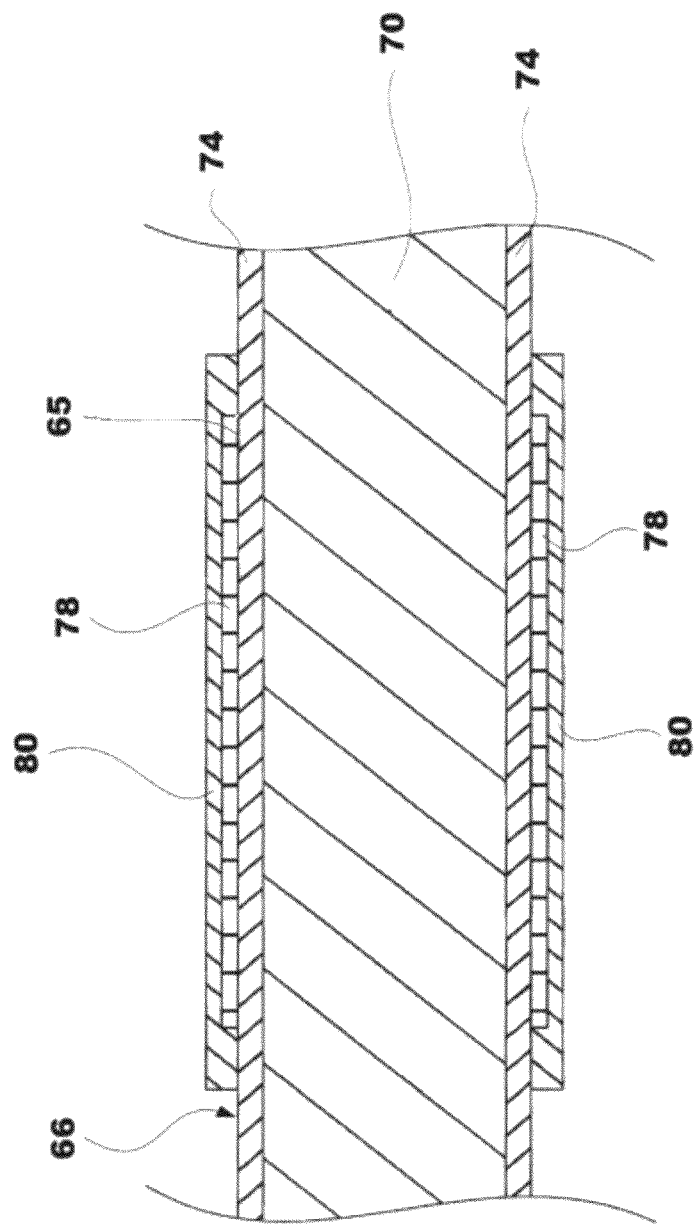
FIG. 1A shows a close-up cross-sectional view of a portion of a tip of the thermal surgical tool system of FIG. 1.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

As used herein, the term "ferromagnetic," "ferromagnet," and "ferromagnetism" refers to any ferromagnetic-like material that is capable of producing heat via magnetic induction, including, but not limited to, ferromagnets and ferrimagnets. It is not intended that such materials must be heated exclusively by magnetic induction unless otherwise indicated and such may acquire heat from resistive heating, eddy currents, etc., in addition to magnetic induction. The term "ferromagnetic conductor" refers to a conductor having one or more layers of ferromagnetic material disposed in electrical communication with the conductor, such that passage of electrical energy through the conductor causes substantially uniform heating of the ferromagnetic material sufficient to produce a desired therapeutic tissue effect.

Turning now to FIG. 1, there is shown a perspective view of a thermal surgical instrument system, generally indicated at 10. As will be discussed in additional detail below, the thermal instrument system preferably uses a ferromagnetic coated conductor to treat or destroy tissue (e.g. endothelial tissue welding, homeostasis, ablation, etc).

It will be appreciated that the thermal surgical instrument uses heat to incise tissue and does not cut tissue in the sense of a sharp edge being drawn across the tissue as with a conventional scalpel. While the embodiments of the present invention could be made with a relatively sharp edge so as to form a cutting blade, such is not necessary as the heated element discussed herein will separate tissue without the need for a cutting blade or sharp edge. However, for convenience, the term cutting is used when discussing separating tissue.

In thermal surgical instrument system 10, a control mechanism, such as a foot pedal 20 is used to control output energy produced by a power subsystem 30. The energy from the power subsystem 30 may be sent via radio frequency (RF) or oscillating electrical energy along a cable 40 to a handheld surgical tool 50, which contains a conductor 60 having a section thereof circumferentially coated with a ferromagnetic coating 65. The ferromagnetic coating 65 may transfer the electrical energy into available thermal energy via induction and corresponding hysteresis losses in the ferromagnetic material disposed around a conductor wire 66. (While conductor wire is used for ease of reference, it will be appreciated that the conductor material need not be a wire and those skilled in the art will be familiar with multiple conductors which will work in light of the disclosure of the present invention.)

Application of a magnetic field (or magnetizing) to the ferromagnetic coating may produce an open loop B-H curve (also known as an open hysteresis loop), resulting in hysteresis losses and the resultant thermal energy. Electrodeposited films, such as a nickel-iron coating like PERMALLOY™, may form an array of randomly aligned microcrystals, resulting in randomly aligned domains, which together may have an open loop hysteresis curve when a high frequency current is passed through the conductor.

The RP energy may travel along the conductor's surface in a manner known as the "skin effect". The current density is generally greatest at the surface and decreases in magnitude farther into the material where the electric field approaches zero. The depth at which the skin effect current is reduced to about 37 percent of its surface value is referred to as the skin depth and is a function of the electrical resistivity, the magnetic permeability of the material conducting the current, and the frequency of the applied alternating RF current. The alternating RF current in the conductor's surface induces generally uniform heating at the location of the ferromagnetic coating.

The alternating RF current in the conductor's surface produces an alternating magnetic field, which may excite the domains in the ferromagnetic portion 65. As the domains realign with each oscillation of the current, hysteresis losses in the coating may cause inductive heating. Heating of the ferromagnetic portion 65 due to hysteresis loss ceases above its Curie point because the material loses its magnetic properties. Additionally, because the relative permeability of the ferromagnetic portion 65 changes in response to temperature, the associated skin depth also changes, and therefore the amount of current conduction through the skin layer undergoes a transition near the Curie point. Thus, heating of the ferromagnetic portion 65 due to resistive heating may also be reduced as it approaches the Curie point.

The ferromagnetic material 65 may have a Curie temperature. A Curie temperature is the temperature at which the material becomes paramagnetic, such that the magnetic properties of the coating are lost. When the material becomes paramagnetic, the ferromagnetic heating may be significantly reduced or even cease. Theoretically, this should cause the temperature of the ferromagnetic material 65 to stabilize around the Curie temperature if sufficient power is provided to reach the Curie temperature. However, it has been found that the temperature of the ferromagnetic material 65 may exceed its calculated Curie temperature under certain operational conditions. It has been observed that if sufficient power has been applied, the tip temperature can continue to rise due to resistive heating in the overall conductor and the tip can potentially exceed the Curie temperature. When this occurs, an increase in current is observed while operating at a constant power level. It is believed that this may be due, at least in part to an increase in the skin depth and a resulting drop in impedance above the Curie temperature. The increase may also be due to the resistance of the ferromagnetic coating dropping which in turn raises the current level for a fixed power level. The increased current may then cause more resistive heating in the non-ferromagnetic portion of the conductor. Thus, it may be preferable to have a high conductivity in the conductor.

The RF conductor from the signal source up to and including the tip, may form a resonant circuit at a specific frequency (also known as a tuned circuit). Changes in the tip "detune" the circuit. Thus, should the ferromagnetic coating 65 or the conductor 66 become damaged, the circuit may likely become detuned. This detuning should reduce the efficiency of the heating of the ferromagnetic material 65 such that the temperature will be substantially reduced. The reduced temperature should ensure little or no tissue damage after breakage.

It should be understood that the handheld surgical instrument 50 may include indicia of the power being applied and may even include a mechanism for controlling the power. Thus, for example, a series of lights 52 could be used to indicate power level, or the handheld surgical instrument 50 could include a switch, rotary dial, set of buttons, touchpad or slide 54 that communicates with the power source 30 to regulate power and thereby affect the temperature at the ferromagnetic material 65 to have varying effects on tissue. While the controls are shown on the foot pedal 20 or the handheld surgical instrument 50, they may also be included in the power subsystem 30 or even a separate control instrument. Safety features such as a button or touchpad that must be contacted to power the handheld surgical instrument 50 may be employed, and may include a dead man's switch.

The thermal surgical instrument system 10 allows the power output to be adjustable in order to adjust the temperature of the instrument and its effect on tissue. This adjustability gives the surgeon precise control over the effects that may be achieved by the handheld surgical instrument 50. Tissue effects such as cutting, hemostasis, tissue welding, tissue vaporization and tissue carbonization occur at different temperatures. By using the foot pedal 20 (or some other user control, such as a dial 32 on the power subsystem 30) to adjust the power output, the surgeon (or other physician, etc.) can adjust the power delivered to the ferromagnetic coating 65 and consequently control the tissue effects to achieve a desired result. The foot pedal 20 may also be configured only to provide on and off, with the dial controlling power level.

Thermal power delivery can be controlled by varying the amplitude, frequency or duty cycle of the alternating current waveform, or alteration of the circuit to affect the standing wave driving the ferromagnetic coated conductor, which may be achieved by input received by the foot pedal 20, the power subsystem 30, or the controls on the handheld surgical instrument 50.

One additional advantage achieved by ferromagnetic heating is that the ferromagnetic material can be heated to a cutting temperature rapidly. In some instances the ferromagnetic material 65 can be heated in a small fraction of a second (e.g. as short as one quarter of a second). Additionally, because of the relatively low mass of the coating, the small thermal mass of the conductor, and the localization of the heating to a small region due to construction of the handheld surgical instrument 50, the material may also cool extremely rapidly (e.g. in some instances approximately one half of a second). This provides a surgeon with a precise thermal instrument while reducing accidental tissue damage caused by touching tissue when the thermal instrument is not activated.

It will be appreciated that the time period required to heat and cool the handheld surgical instrument 50 will depend, in part, on the relative dimensions of the conductor 66 and the ferromagnetic material 65 and the heat capacity of the structure of the surgical instrument. For example, the above time periods for heating and cooling of the handheld surgical instrument 50 may be achieved with a tungsten conductor having a diameter of about 0.375 mm and a ferromagnetic coating of a Nickel Iron alloy (such as NIRON™ available from Enthone, Inc. of West Haven, Conn.) about the tungsten conductor about 0.0375 mm thick and two centimeters long.

One advantage of the present invention is that a sharp edge is not needed. When power is not being supplied to the surgical instrument, the instrument will not inadvertently cut tissue of the patient or of the surgeon if it is dropped or mishandled. If power is not being supplied to the conductor 66 to cause heating of the ferromagnetic material 65, the "cutting" portion of the instrument quickly cools and may be touched without risk of injury. This is in sharp contrast to a cutting blade which may injure the patient or the surgeon if mishandled. Another advantage of the present invention is that the ferromagnetic heating along the coated section of the conductor is generally uniform and capable of producing a uniform hemostatic effect along the entire section of ferromagnetic material 65 in contact with tissue.

Additions may be placed on the handpiece in various locations. These may include a sensor stem 12 including a sensor to report temperature or a light to illuminate the surgical area.

Turning now to FIG. 1A, there is shown a cross-sectional view of a portion of a surgical tip having a conductor 66, such as a conductor wire, in accordance with one aspect of the invention. It may be desirable that the conductor 66 has a relatively small diameter or cross-section so as to make precise cuts in tissue, or other materials. However, it is also desirable to have the conductor 66 be relatively stiff and resist bending when encountering tissue, such as when resecting a tumor or other tissue. To accomplish these ends, the conductor 66, as shown in FIG. 1, may be comprised of a material with a Young's Modulus sufficient to resist bending during use and/or the conductor 66 may include a support 70, as shown in FIG. 1A, which will resist bending even when the support has a fairly small diameter or cross-section. Examples of metals having this property may include tungsten, titanium, stainless steel, Haynes 188, Haynes 25, etc.

In addition to the Young's Modulus of the support 70, other properties of the material used for the support 70 may be important. These properties may include the resistivity of the material, the thermal and electrical conductivity of the material, the material's heat capacity, the material's coefficient of thermal expansion, the annealing temperature of the material, and the ability to plate a second material to the material comprising the support 70.

In choosing a material to use as the support 70, it may be important that such material have the greatest amount of resistance to bending while having low resistivity to minimize heating of the conductor 66 due to resistance heating. Additionally, it may also be important that the material have a low heat capacity so that heat is not stored in the conductor 66 thus allowing the surgical tip to cool rapidly when not being used. This may help limit or prevent collateral damage to structures adjacent the surgical site.

Additionally, it is desirable that the support 70 be comprised of material having a sufficiently high annealing temperature. At times, the surgical tip may be operated at temperatures, for example, between about 400 and 600 degrees Celsius. Thus, to avoid alterations in the properties of the support 70, the annealing temperature of the material used as the support 70 should be sufficiently higher than the expected operating ranges of the surgical tip.

Furthermore, it may be desirable that the support 70 be comprised of a material having a coefficient of thermal expansion value that is close to the coefficient of thermal expansion of the ferromagnetic material 65, such as a ferromagnetic coating 78, to facilitate plating of the ferromagnetic coating 78 to the support 70 in some configurations.

It has been observed, however, that some materials having adequate resistance to bending (Young's modulus) during normal operation of the surgical tip may have a coefficient of thermal expansion that is too low for adequate plating integrity. Thus, one or more intervening layers having an intermediate coefficient of thermal expansion may be plated on the conductor 66 (FIG. 1) or the support 70 and then the ferromagnetic layer 65 plated on the one or more intervening layers to provide for a transition to accommodate the difference between the coefficients of thermal expansion of the support 70 and the ferromagnetic material 65, as described in more detail below.

Another important factor regarding the material used for the support 70 is its ability to conduct electricity. There are multiple materials which provide adequate support, but which are not sufficiently conductive. Thus a conductor 66 may be comprised of multiple layers of different material so as to minimize any undesirable property or properties of the support 70.

For example, the support 70 may be conductive or non-conductive, and may have a one or more conductive intervening layers 74 disposed thereon, such as copper, silver, etc., or other conductive material. The intervening layer allows the energy to pass without significant resistive heating, thus allowing the tip to cool down more rapidly. (It will be appreciated that the cross-sectional view of FIG. 1A is not necessarily to scale and the support may be much larger in diameter than the thickness of the other layers discussed herein. Moreover, it will be appreciated that the conductive intervening layer 74 may extend the entire length of the conductor 66 as will be discussed in more detail below.)

The material or substrate used as the support 70 may have an optimal thermal conductivity to allow for conductive cooling of the surgical tip when energy is not being delivered to the conductor 66. Furthermore, the support 70 will have a sufficiently high Young's modulus to resist bending when the surgical tool is being used to provide a thermal therapeutic effect to tissue during a procedure. For example, the support 70 may be comprised of a material having a Young's Modulus (modulus of elasticity) of greater than 17 psi (118 GPa). According to one aspect of the invention, the support 70 may be comprised of a material having a Young's Modulus of about 58 psi (400 GPa) or greater, such as tungsten.

Furthermore, it is desirable that the intervening layer 74 be readily attachable to the support 70. This may be accomplished by using a substrate as the support 70 that allows for electroplating of the intervening layer 74 thereto under reasonable commercial standards. For example, the substrate may be easily deoxidized ("activated") to facilitate plating of the intervening layer 74 to the support 70.

The one or more conductive intervening layers 74 may comprise a variety of materials, such as copper, silver, etc., having desired properties. The intervening layer 74 may be disposed along a portion of the support or substantially extend along the entire length of the support 70. An important property of the intervening layer 74 is that it be a good electrical conductor having low resistivity such that heating due to the resistance of the intervening layer 74 is minimized. Furthermore, it is desirable in some configurations that one of the intervening layer(s) 74 not only be readily attachable to the support 70, but also be a good substrate for attaching the ferromagnetic material 65, such as a ferromagnetic layer or coating 78 thereto. Like the support 70, this may be accomplished by using a substrate as the intervening layer 74 that allows for electroplating of a ferromagnetic coating 78 thereto under reasonable commercial standards, such as a substrate that is easily activated to facilitate plating of the ferromagnetic layer 78.

Another important property of the intervening layer 74 in some configurations may be malleability. If the coefficient of thermal expansion of the intervening layer 74 differs significantly from the coefficient of thermal expansion of the support 70, the intervening layer 74 may have to be sufficiently malleable so that the integrity of the intervening layer 74 is not easily compromised when subjected to the thermal conditions under which the surgical tip is operated. For example, a surgical tip including an intervening layer 74 comprised of copper having a linear coefficient of thermal expansion of approximately 17 µm/° C. attached to a support 70 comprised of tungsten having a linear coefficient of thermal expansion of approximate 4.5 µm/° C. may be sufficient to withstand the heat variability that the surgical tip undergoes under normal operation.

The conductor 66 of FIG. 1 also shows a ferromagnetic layer 65 disposed adjacent to the intervening layer 74. As discussed above, the ferromagnetic layer 65 may be plated on the intervening layer 74. The ferromagnetic material 65 may be located along a portion of the conductor 66 at a defined location (or locations) so as to provide for localized heating along the surgical tip only in an area where heating is desired. For example, the ferromagnetic layer or coating 78 may be located along less than about 90%, 50%, 10%, etc. of the length of the conductor 66 so as to provide localized heating in a desired area. In other words, the length which the ferromagnetic material extends may be less than the length of the conductor 66. The ferromagnetic coating 78 may have high permeability to facilitate inductive or other ferromagnetic heating of the ferromagnetic material, such as NIRON™, PERMALLOY™, Co, $CrO_2$, etc. Additionally, the ferromagnetic coating 78 may have a relatively high thermal conductance and low heat capacity to facilitate rapid heating and cooling of the surgical tip.

According to one aspect of the invention the surgical tip may include a ferromagnetic material 65 having a coefficient of thermal expansion that varies significantly from the coefficient of thermal expansion of the support 70. Such a surgical tip may also include at least one intervening layer 74 having a coefficient of thermal expansion with an intermediate value to accommodate the differences in the coefficient of thermal expansions of the ferromagnetic layer 65 and the support 70. Such a configuration may help maintain the integrity of the surgical tip under expected operating conditions.

The ferromagnetic layer 65 may be exposed or may be covered with an exterior coating 80 made from a biocompatible material to ensure that there is no reaction between the ferromagnetic layer 65 and the patient tissues. The exterior coating 80 may also act as a lubricant between the surgical tip and tissue which is being treated by reducing the attachment of biologic tissues to the surgical tip. For example, the exterior coating 80 may be titanium nitride (or one of its variants), TEFLON or a host of other biocompatible materials.

The exterior layer 80 may also act as an oxygen barrier to prevent oxidation of the layer of ferromagnetic material 65, any intervening layer 74, and/or the support 70. For example, it has been observed that oxidation of the support 70 may cause the support 70 to become brittle making the support 70 more susceptible to damage. It will be appreciated that the exterior layer 80 may be disposed on the conductor 66 so as to substantially cover the ferromagnetic layer 65 and the entire conductor 66. Alternatively, the exterior layer may be disposed on the conductor 66 so as to cover the ferromagnetic layer 65 and only a portion of the conductor 66.

According to one aspect of the invention, a conductor 66 (such as the one shown in FIG. 1A) may comprise a support 70 having a diameter of about 500-750 μm, an intervening layer 74 having a cross-sectional thickness of about 20-50 μm (or about 2-5 skin depths), and a ferromagnetic material 65 (e.g. a coating 78) having a cross-sectional thickness of about 2-10 μm. The thickness of the ferromagnetic material 65 forming the coating 78 may be selected as a function of the skin depths of the intervening layer 74, or the combined skin depths of multiple intervening layers if such are included in a surgical tip as described below. The antioxidation layer may be very thin, such as 1-3 μm.

Figure 1B:
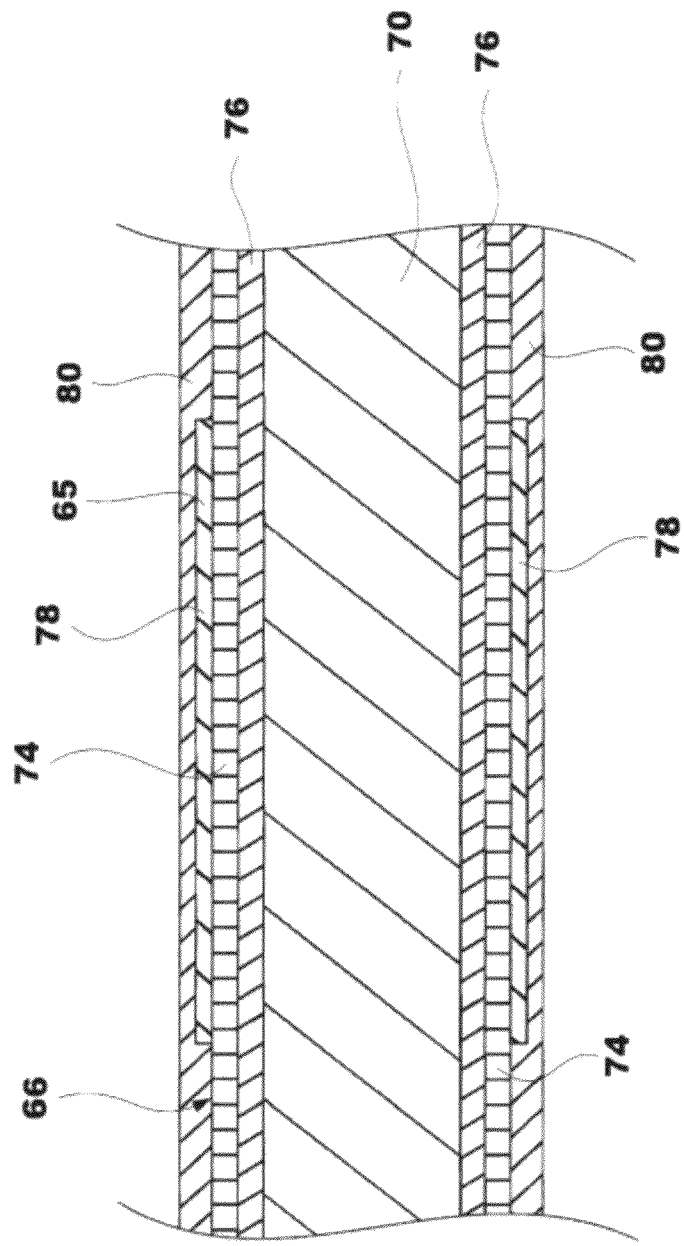
FIG. 1B shows a close-up cross-sectional view of a portion of another tip according to principles of the present invention.

Turning now to FIG. 1B, there is shown a close-up cross-sectional view of a portion of another surgical tip according to principles of the present invention. The tip in FIG. 1B is similar to the tip in FIG. 1A with the addition of a second intervening layer 76. The second intervening layer 76 may be a strike layer, such as nickel strike or gold flash, for facilitating plating of the first intervening layer 74 to the support. The second intervening layer 76 may be relatively thin, for example, about 1-2 μm. The second intervening layer 76 may provide for better attachment or bonding of the first intervening layer 74 to the support 70.

The second intervening layer 76 may have a coefficient of thermal expansion which provides a transition to accommodate any differences in the coefficient of thermal expansions between the support 70 and the ferromagnetic material 65 (typically a ferromagnetic coating 78), and any other intervening layers, such as the first intervening layer 74. It will be appreciated that taking into account the coefficients of thermal expansion of the different layers which may be used in constructing a surgical tip of the present invention may increase the durability of the surgical tip. It will also be appreciated that additional intervening layers, other than those shown, may be included to further provide for a more gradual transition of coefficients of thermal expansion between layers. For example, the conductor 66 may include a strike layer in addition to multiple intervening layers.

Figure 1C:
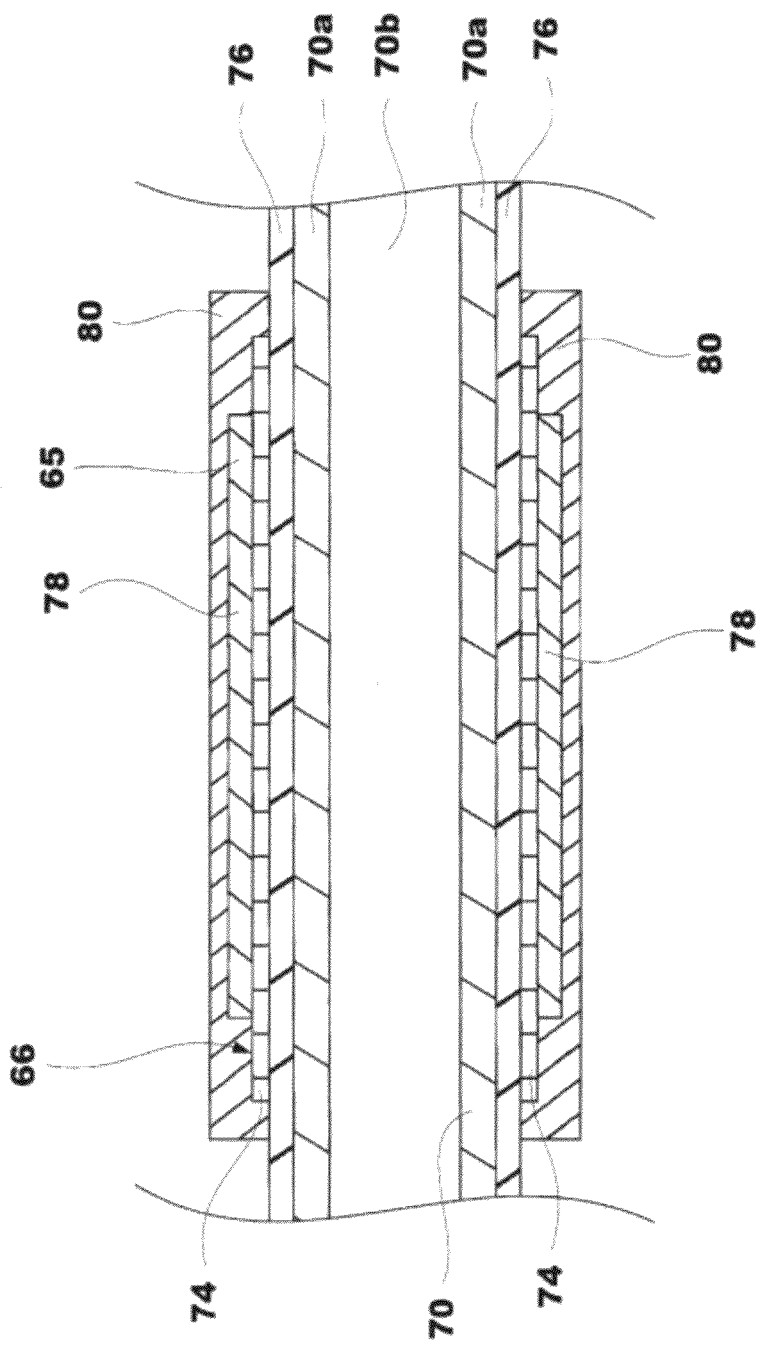
FIG. 1C shows a close-up cross-sectional view of a portion of another tip according to principles of the present invention.

Turning now to FIG. 1C, there is shown a close-up cross-sectional view of a portion of another surgical tip according to principles of the present invention. The surgical tip may comprise a conductor 66 having a support 70 that is tubular. Thus, in the cross-sectional view the wall 70a which circumscribes a void 70b of the support 70 can be seen. By using a tubular support 70 the amount of material comprising the support 70 is reduced. Thus, the heat capacity of the tubular support 70 will be reduced allowing the surgical tip to cool more rapidly. While the conductor 66 is shown as being generally linear, it will be appreciated that the conductor can be formed into a variety of shapes.

Figure 1D:
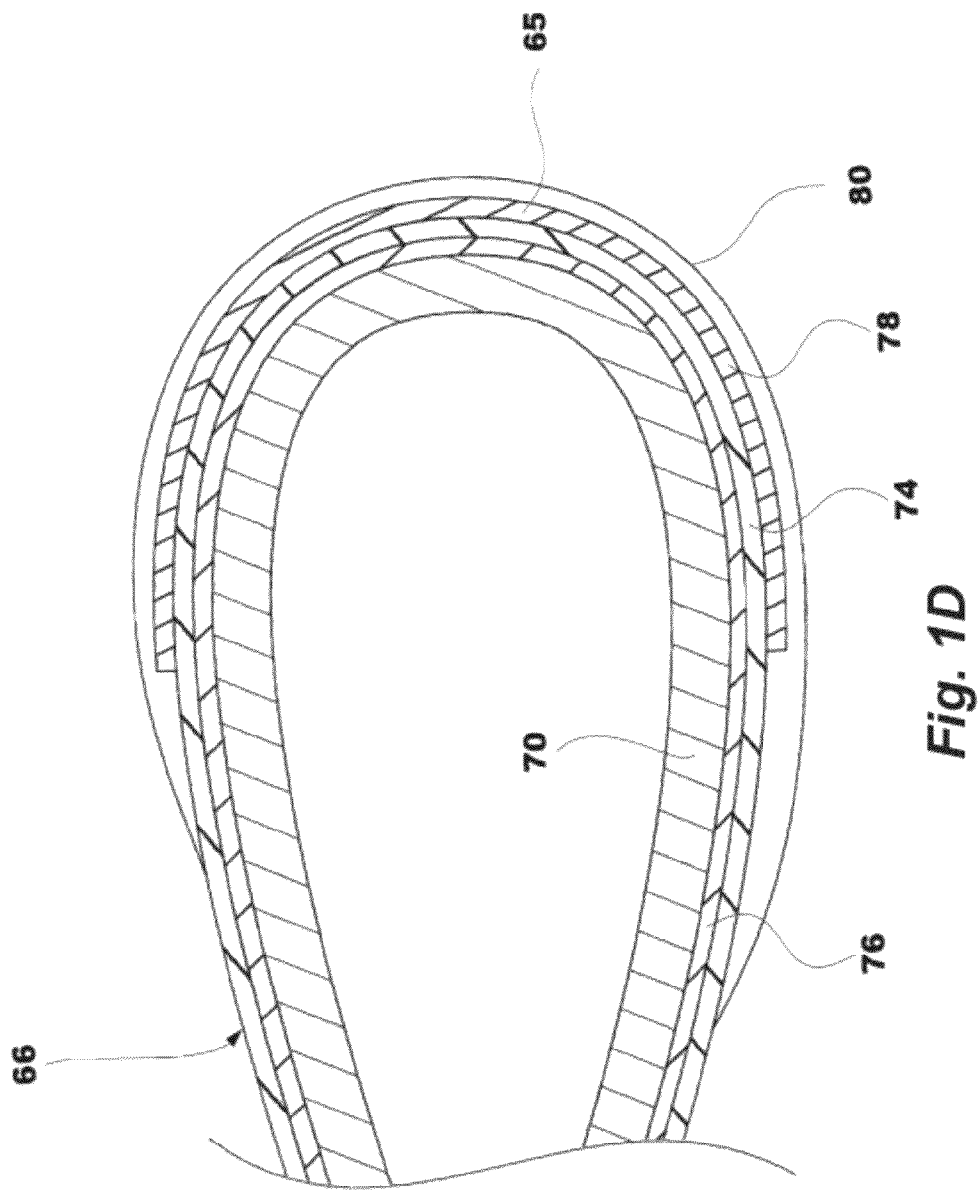
FIG. 1D shows a fragmented cross-sectional view of a tip having a loop geometry.

FIG. 1D shows a fragmented cross-sectional view of a portion of a surgical tip having loop geometry. As with the surgical tips shown in FIGS. 1A-1C, the surgical tip in FIG. 1D may include a conductor 66 having one or more intervening layers, a ferromagnetic material, and a biocompatible layer disposed thereon. (For ease of illustration the multiple layers are shown disposed on one side of the support 70, but it will be appreciated that one or more of the multiple layers shown may be circumferentially disposed on the support 70). The various layers which make up the surgical tip may be disposed on and extend along the support 70 at various lengths. For example, the second intervening layer 76 may substantially extend the entire length of the support 70. Likewise, the first intervening layer 74 (and/or any additional intervening layers) and a biocompatible layer 80 may substantially extend along the entire length of the support 70. In the alternative, the first intervening layer 74 and the biocompatible layer 80 may extend a short distance beyond the ferromagnetic material 65.

As discussed above, the ferromagnetic material 65 may be disposed along only a portion of the conductor 66 at a defined location (or locations) so as to provide for localized heating along the surgical tip only in an area(s) where heating is desired. As described in more detail below, different tips may be constructed having ferromagnetic material 65 which extend different lengths along a conductor 66 extending exteriorly from a surgical handpiece. Thus, one tip may have a ferromagnetic material 65 which extends only along the distal end of the exterior portion of the conductor 66, whereas another tip may have a ferromagnetic material 65 which extends substantially the entire length of the exterior portion of the conductor 66. Additionally, the exterior portion of the conductor 66 may be constructed in a variety of shapes wherein the ferromagnetic material 65 substantially conforms to the shape of the conductor 66.

Figure 2:
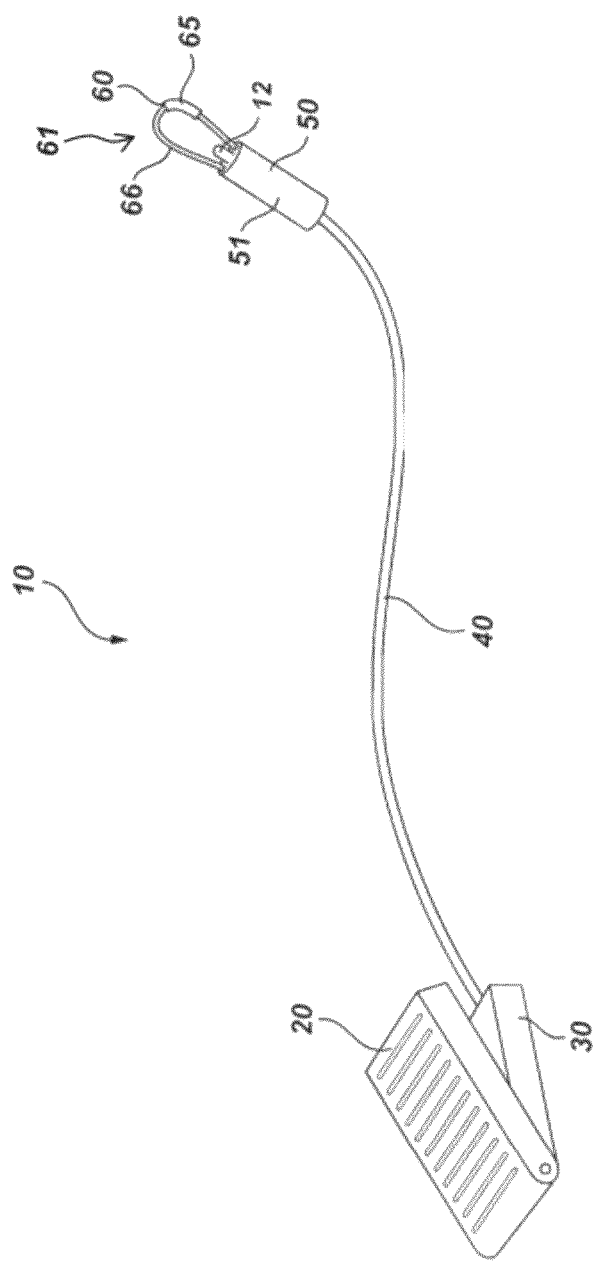
FIG. 2 shows a perspective view of an alternate embodiment of a thermal surgical instrument system in accordance with the present invention.

Turning now to FIG. 2, a perspective view of another aspect of a thermal surgical system 10 made according to principles of the present invention is shown. In FIG. 2, the power source 30 is contained within the foot pedal 20. Depending on the application and power required, the instrument may even be entirely battery powered for relatively low power applications. An alternate embodiment for low power requirements may include the battery, power adjustment and power delivery, all self-contained in the handle 51 of the handheld surgical instrument 50. Furthermore, a wireless communication module can be employed to send and receive information from the handheld surgical instrument 50, including status and control settings that would enable users to monitor system performance and alter power settings remotely from the handheld surgical instrument 50 itself.

It is our understanding that this thermal solution may provide advantages over monopolar and bipolar electrical systems currently available because the thermal damage may remain very close to the ferromagnetic surface of the coated region, whereas monopolar and bipolar electrical tissue ablation may frequently cause tissue damage for a distance away from the point of contact. It is our understanding that this method may also overcome disadvantages of other thermal devices that rely on resistive heating which may require more time to heat and cool and thus present greater patient risk, while potentially having higher voltage requirements at the point of heating.

Furthermore, the thin ferromagnetic coating 65, which may be disposed along a small segment of the conductor, may reduce the heating of other non-target material in the body, such as blood when working within the heart in atrial ablation—which can lead to complications if a clot is formed. The small thermal mass of the conductor 66, and localization of the heating to a small region provided by the construction of the instrument (i.e. ferromagnetic material 65 and adjacent structures) provides a reduced thermal path for heat transfer in directions away from the location of the ferromagnetic material 65. This reduced thermal path may result in the precise application of heat at only the point desired. As this technology alone does not employ a spark or an arc like monopolar or bipolar technology, risks of ignition of, for example, anesthetic gasses within or around the patient are also reduced.

The thermal surgical instrument system 10 may be used for a variety of therapeutic means—including sealing, "cutting" or separating tissue, coagulation, or vaporization of tissue. In one configuration, the thermal surgical instrument system 10 may be used like a knife or sealer, wherein the surgeon is actively "cutting" or sealing tissue by movement of the ferromagnetic material 65 through tissue. The thermal action of the embodiments disclosed herein may have distinct advantages including substantial reduction, if not elimination, of deep tissue effects compared with those associated with monopolar and bipolar RF energy devices.

In another configuration, the conductor 66 having a ferromagnetic material 65 disposed thereon may be inserted into a lesion and set to a specific power delivery or variable power delivery based on monitored temperature. The thermal effects on the lesion and surrounding tissue may be monitored until the desired thermal effect is achieved or undesired effects are noticed. One advantage of using the conductor 66 having a ferromagnetic material 65 is that it may be more cost effective compared to using microwave or thermal laser modalities and avoids the undesired tissue effects of microwave lesion destruction. Thus, for example, a surgeon can contact a tumor or other tissue to be destroyed with the ferromagnetic material 65 and precisely control treatment while reducing or even eliminating unwanted tissue damage when the handheld surgical instrument 50 is activated.

Sensors may be used to monitor conditions of the handheld surgical instrument 50 or the tissue, such as an infrared detector or sensor stem 12. For instance, the temperature of the device or tissue may be important in performing a procedure. A sensor in the form of a thermocouple, a junction of dissimilar metals, thermistor or other temperature sensor may detect the temperature at or near the ferromagnetic coating 65 or tissue. The sensor may be part of the device, such as a thermocouple formed as a part of the conductor or near the ferromagnetic coating, or separate from the handheld surgical instrument 50, such as a separate tip placed near the tissue or ferromagnetic coating 65. The temperatures may also be correlated with tissue effects, seen in FIG. 15. Other useful conditions to monitor may include, but are not limited to, color, spectral absorption, spectral reflection, temperature range, water content, proximity, tissue type, transferred heat, tissue status, impedance, resistance, voltage and visual feedback (e.g. a camera, fiberoptic or other visualization device).

The handheld surgical instrument 50 may be configured for repeat sterilization or single patient uses. More complex devices may be useful for repeat sterilization, while more simple devices may be more useful for single patient use.

A method for treating or cutting tissue may include the steps of: selecting a surgical instrument having a cutting edge and a conductor disposed adjacent the cutting edge, at least a portion of which is coated with a ferromagnetic material; cutting tissue with the cutting edge; and applying oscillating electrical energy to the conductor to heat the ferromagnetic material and thereby treating the cut tissue.

Optional steps of the method may include the steps of: causing hemostasis within the cut tissue; using the heated ferromagnetic material to incise tissue; or using the heated ferromagnetic material to cause vascular endothelial welding.

Figure 3:
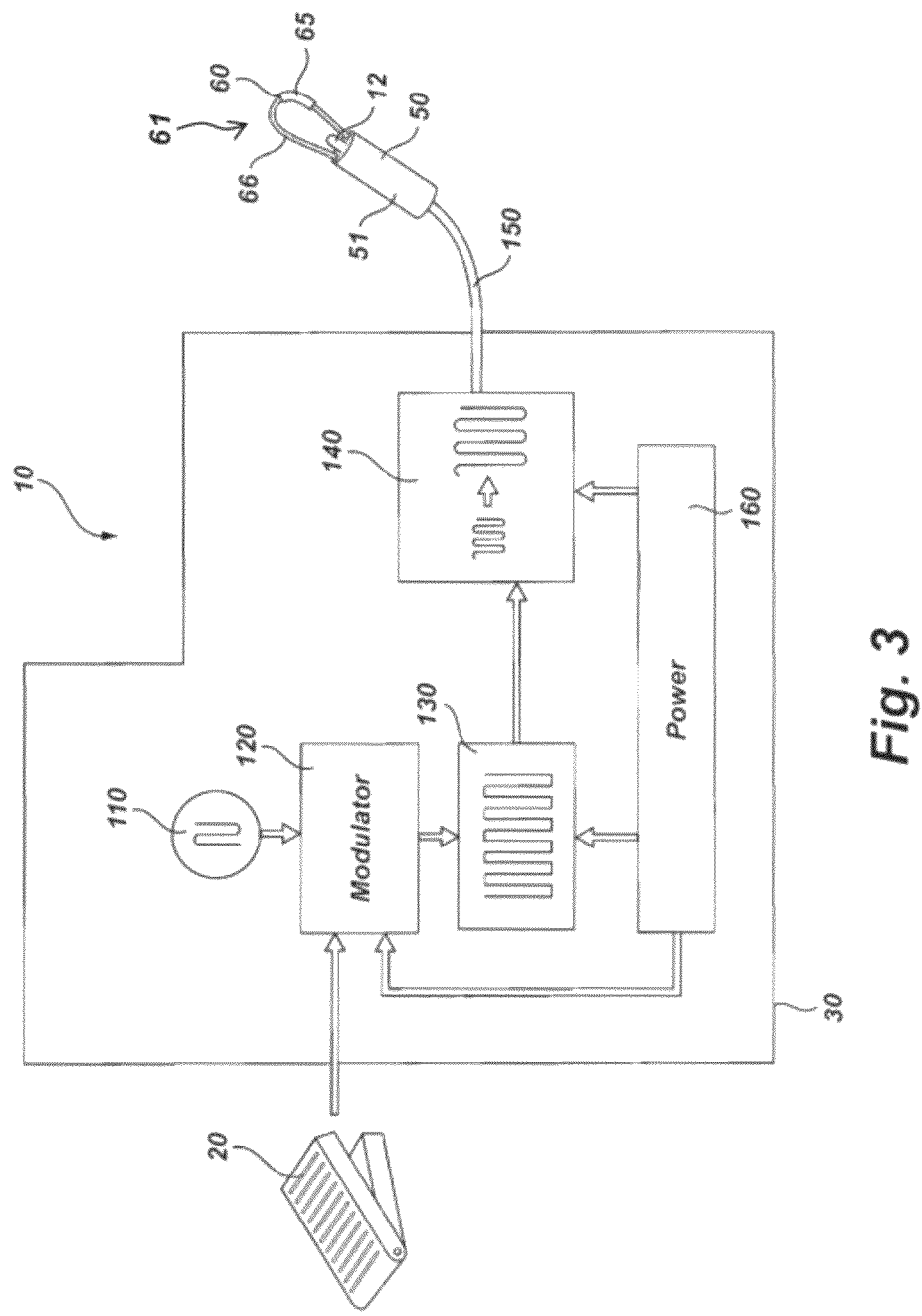
FIG. 3 shows a diagram of a thermal surgical instrument system in accordance with the principles of the present invention.

Referring now to FIG. 3, a diagram of an embodiment of the adjustable thermal surgical instrument system 10 is shown. The power delivery to the ferromagnetic coating 65 is controlled by a modulated high frequency waveform. The modulated waveform allows power delivery to be controlled in a manner that adjustably modifies, allows or blocks portions of the waveform based on the desired power delivery.

In FIG. 3, an initial waveform 110 is passed through a modulator 120 receiving commands from a control device, such as a foot pedal 20. The waveform is created by an oscillator 130 to the desired frequency and modulated by the modulator 120, which may include, but is not limited to, one or more of amplitude, frequency or duty cycle modulation, including a combination thereof. The resultant signal is then amplified by an amplifier 140. The amplified signal is sent across a tuned cable 150, meaning that the cable is tuned to provide a standing wave with maximum current and minimum voltage at the location of the ferromagnetic material 65 of the handheld surgical instrument 50. Alternatively, the cable 150 may not be tuned, but a circuit may be placed in the handle 51 to impedance match the load of the surgical tip 61 to the power source 30.

The thermal surgical instrument system 10 may be tuned by specifying the location of the ferromagnetic material 65 with respect to the amplifier 140 (such as cable length) and tuning the high frequency signal to approximately a resonant standing wave such that current is maximized at the location of the ferromagnetic material 65.

It should be recognized that the surgical instrument may operate in a dynamic environment. Thus when used herein, approximately a standing wave means that a circuit may be tuned such that the signal may be near an optimal standing wave but may not achieve it, may only achieve the wave for small amounts of time, or may successfully achieve a standing wave for longer periods of time. Similarly, any use of "standing wave" without the modifier of approximate should be understood to be approximate in the context of the thermal surgical instrument of the present invention.

One method for achieving such current maximization is to connect the conductor 66 to a cable 150 that is an odd multiple of one-quarter wavelengths in length and connected to the output of the amplifier 140. The design of the circuit having a resonant standing wave is intended to optimize power delivery to the ferromagnetic coating. However, in one embodiment, the power source 30 could be positioned at the location of (or closely adjacent to) the ferromagnetic material 65, and tuning could be achieved with electrical components, all within a single handheld, battery-powered instrument. Alternatively, electrical components necessary for impedance matching can be located at the output stage of the amplifier 140. Further, electrical components, such as a capacitor or inductor, can be connected in parallel or series to the ferromagnetic coated conductor 60 at the location of the connection of the conductor 66 to the cable 150, in order to complete a resonant circuit.

Dynamic load issues can be caused by the interaction of the surgical tip with various tissues. These issues may be minimized by the standing current wave being maximized at the load location. Multiple different frequencies can be used, including frequencies from 5 megahertz to 24 gigahertz, preferably between 40 MHz and 928 MHz. In some regulated countries it may be preferable to choose frequencies in the ISM bands such as bands with the center frequencies of 6.78 MHz, 13.56 MHz, 27.12 MHz, 40.68 MHz, 433.92 MHz, 915 MHz, 2.45 GHz, 5.80 GHz, 24.125 GHz, 61.25 GHz, 122.5 GHz, 245 GHz. In one embodiment, the oscillator 130 uses an ISM Band frequency of 40.68 MHz, a class E amplifier 140, and a length of coaxial cable 150, all of which may be optimized for power delivery to a tungsten conductor 66 with a ferromagnetic material 65 having a thickness of between 0.05 micrometer and 500 micrometers disposed thereon, and preferably the ferromagnetic material having a thickness of between 1 micrometer and 50 micrometers. A useful estimate may be to start with a ferromagnetic material 65 having a thickness of about 10% of the diameter of the conductor 66, and a length of about 5 cm. However, the ferromagnetic material 65 may be disposed as far along the length or along multiple regions of the conductor 66 if more or less uniform ferromagnetic heating is desired. (The ferromagnetic material 65 may be formed from a Nickel Iron (NiFe) alloy, such as NIRON™ from Enthone, Inc. of West Haven, Conn., or other ferromagnetic coatings, including Co, Fe, FeOFe2O3, NiOFe2O3, CuOFe2O3, MgOFe2O3, MnBi, Ni, MnSb, MnOFe2O3, Y3FeS012, CrO2, MnAs, Gd, Dy, EuO, magnetite, yttrium iron garnet, aluminum, PERMALLOy™, and zinc.)

The size of the conductor, size of the ferromagnetic coating, associated thicknesses, shape, primary geometry, composition, power supply and other attributes may be selected based on the type of procedure and surgeon preferences. For example, a brain surgeon may desire a small instrument in a light handheld package designed for quick application within the brain, while an orthopedic surgeon may require a larger device with more available power for operation on muscle.

The conductor may be formed from copper, tungsten, titanium, stainless steel, platinum and other materials that may conduct electricity. Considerations for the conductor may include, but are not limited to mechanical strength, thermal expansion, thermal conductivity, electrical conduction/resistivity, rigidity, and flexibility. It may be desirable to form the conductor wire 66 of more than one material. Connection of two dissimilar metals may form a thermocouple. If the thermocouple were placed in the vicinity of or within the ferromagnetic material, the thermocouple provides a temperature feedback mechanism for the device. Further, some conductors may have a resistivity that correlates to temperature, which may also be used to measure temperature.

The tuning of the power source 30 may also reduce the amount of high frequency energy radiating into the patient to near zero, as voltage is low, and ideally zero, at the location of the ferromagnetic material 65 disposed on the conductor 66. This is in contrast to monopolar devices, which require a grounding pad to be applied to the patient, or bipolar devices, both of which pass current through the tissue itself. The disadvantages of these effects are well known in the literature.

In many of these embodiments discussed herein, the combination of cable length, frequency, capacitance, inductance, tip geometry, etc. may also be used to adjust efficiency of the surgical instrument by tuning the power source 30 to deliver maximum power to the ferromagnetic coating 65, and therefore, maximum heat to the tissue. A tuned system also provides for inherent safety benefits; if the conductor were to be damaged, the system would become detuned, causing the power delivery efficiency to drop, and may even shut down if monitored by an appropriate safety circuit.

The amount of power delivered to the patient tissue may be modified by several means to provide precise control of tissue effects. The power source 30 may incorporate a modulator 120 for power delivery as described above. Another embodiment uses modification of the magnetic field by altering the geometry of the conductor 66 and/or the ferromagnetic coating 65 through which it passes, such as would be caused by a magnet. Placement of the magnet nearby the ferromagnetic coating 65 would similarly alter the ferromagnetic effect and thereby change the thermal effect.

While modulation has been discussed as a method to control power delivery, other methods may be used to control power delivery. In one embodiment, the output power, and correspondingly the temperature of the instrument, is controlled by tuning or detuning the drive circuit including elements of the surgical tip 61.

Figure 4A:
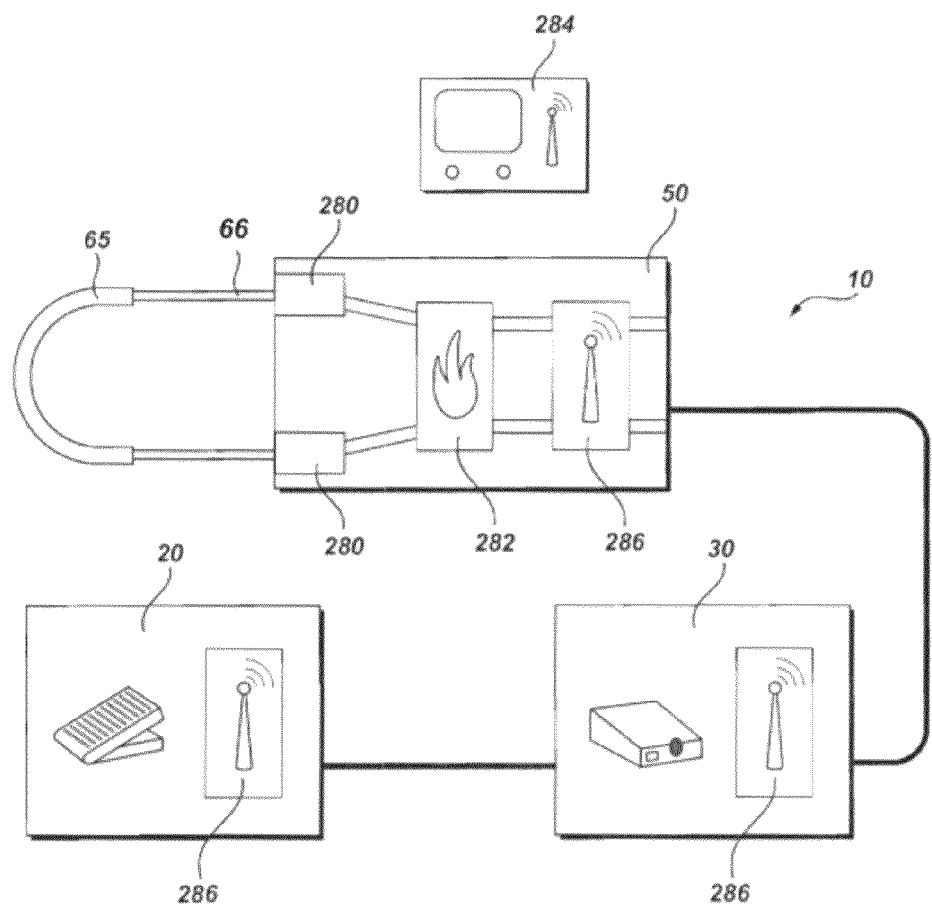
FIG. 4A shows a thermal surgical instrument system with heat prevention terminals, heat sink, and wireless communication devices.

Turning now to FIG. 4A, a thermal surgical instrument system 10 with connectors which attach to opposing first and second ends of a conductor is shown. The conductor as shown in FIG. 4A may be formed by heat prevention terminals 280, such as crimp connectors that provide thermal isolation. One or more heat sinks 282, and wireless communication devices 286 may also be included. The wire conductor 66 may be connected to the handheld surgical instrument 50 by terminals 280 and/or a heat sink 282 at opposing first and second ends of the conductor. Portions of the conductor may extend into the handle into terminals, while the ferromagnetic material 65 disposed on the conductor 66 may extend beyond the handle. The terminals 280 may have a poor thermal conductance such that the terminals 280 reduce the heat transfer from the conductor 66 into the handheld surgical instrument 50. In contrast, the heat sink 282 may draw any residual heat from the terminals 280 and dissipate the heat into other mediums, including the air. Connectors and connections may also be achieved by wire bonding, spot and other welding, in addition to crimping.

Preventing thermal spread may be desirable because the other heated portions of the handheld surgical instrument 50 may cause undesired burns, even to the operator of the handheld surgical instrument 50. In one embodiment, terminals 280 are used to conduct the electric current, but prevent or reduce thermal conduction beyond the exposed portion of the conductor 66.

The thermal surgical instrument may also communicate wirelessly. According to one aspect of the invention, the user interface for monitoring and adjusting power levels may be housed in a remote, wirelessly coupled device 284. The wirelessly coupled device may communicate with a wireless module 286 contained within the thermal surgical instrument system 10, including the handheld surgical instrument 50, the control system (such as footpedal 20), and/or the power subsystem 30. By housing the control interface and display in a separate device, the cost of the handheld surgical instrument 50 portion may be decreased. Similarly, the external device may be equipped with more processing power, storage and, consequently, better control and data analysis algorithms.

Figure 4B:
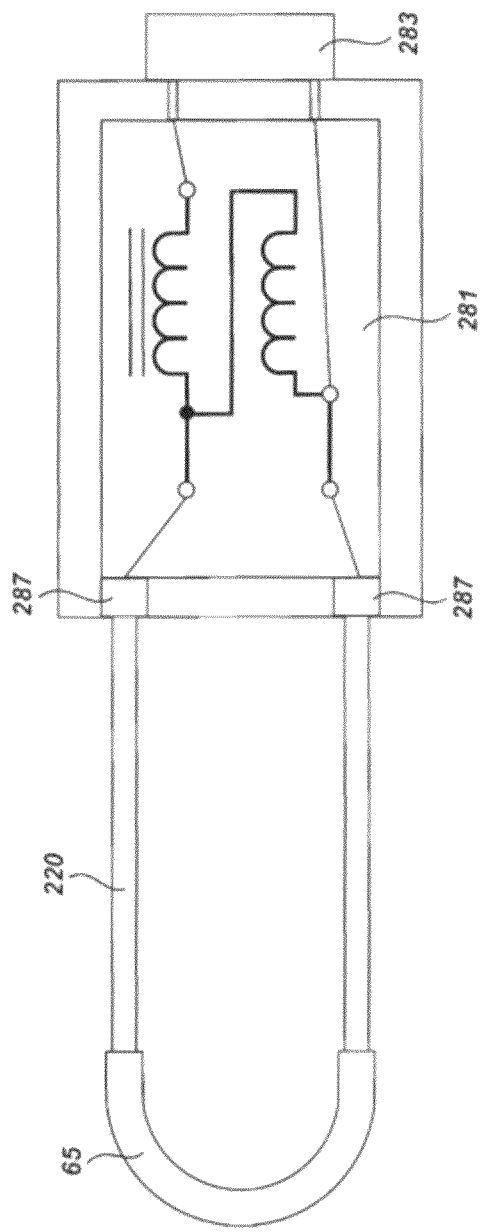
FIG. 4B shows a thermal surgical instrument system with impedance matching network.

Turning now to FIG. 4B, a thermal surgical instrument system with an impedance matching network is shown. The impedance matching network may match the output impedance of the signal source to the input impedance of the load. This impedance matching may aid in maximizing power and minimizing reflections from the load.

According to one aspect, the impedance matching network may be a balun 281. This may aid in power transfer as the balun 281 may match the impedance of the ferromagnetic coated conductor terminals 287 to the amplifier cable terminals 283 (shown here as a coaxial cable connection). In such a configuration, some baluns may be able to act as a heat sink and provide thermal isolation to prevent thermal spread from the thermal energy at the ferromagnetic material 65 transferred by the conductor 66 to terminals 287. The appropriate matching circuitry may also be placed on a ceramic substrate to further sink heat away or isolate heat away from the rest of the system, depending on the composition of the substrate.

It should be recognized that the elements discussed in FIGS. 4A and 4B can be used in conjunction with any of the embodiments shown herein.

Turning now to FIG. 4C, there is shown a portion of a thermal surgical tool system according to principles of the present invention. The thermal surgical tool system may include a conductor 66 comprising a support 70 and one or more intervening layers 74 (including a strike layer 76 shown in FIG. 1B), a ferromagnetic portion 65 (typically formed by a ferromagnetic layer 78), and a biocompatible layer 80. The conductor 66 of the thermal surgical tool system may be attached to a printed circuit board 79. Depending on the material used as the support 70, attachment of the conductor to the printed circuit board 79 may be facilitated by conductively connecting the conductor to the printed circuit board 79 via the intervening layer 74. For example, an intervening layer 74 comprised of copper may be more readily attachable to the printed circuit board 79 than a support comprised of tungsten. Additionally, the support 70 could be attached mechanically and have an intervening layer to connect the conductor 66 to the printed circuit board electrically.

Figure 4D:
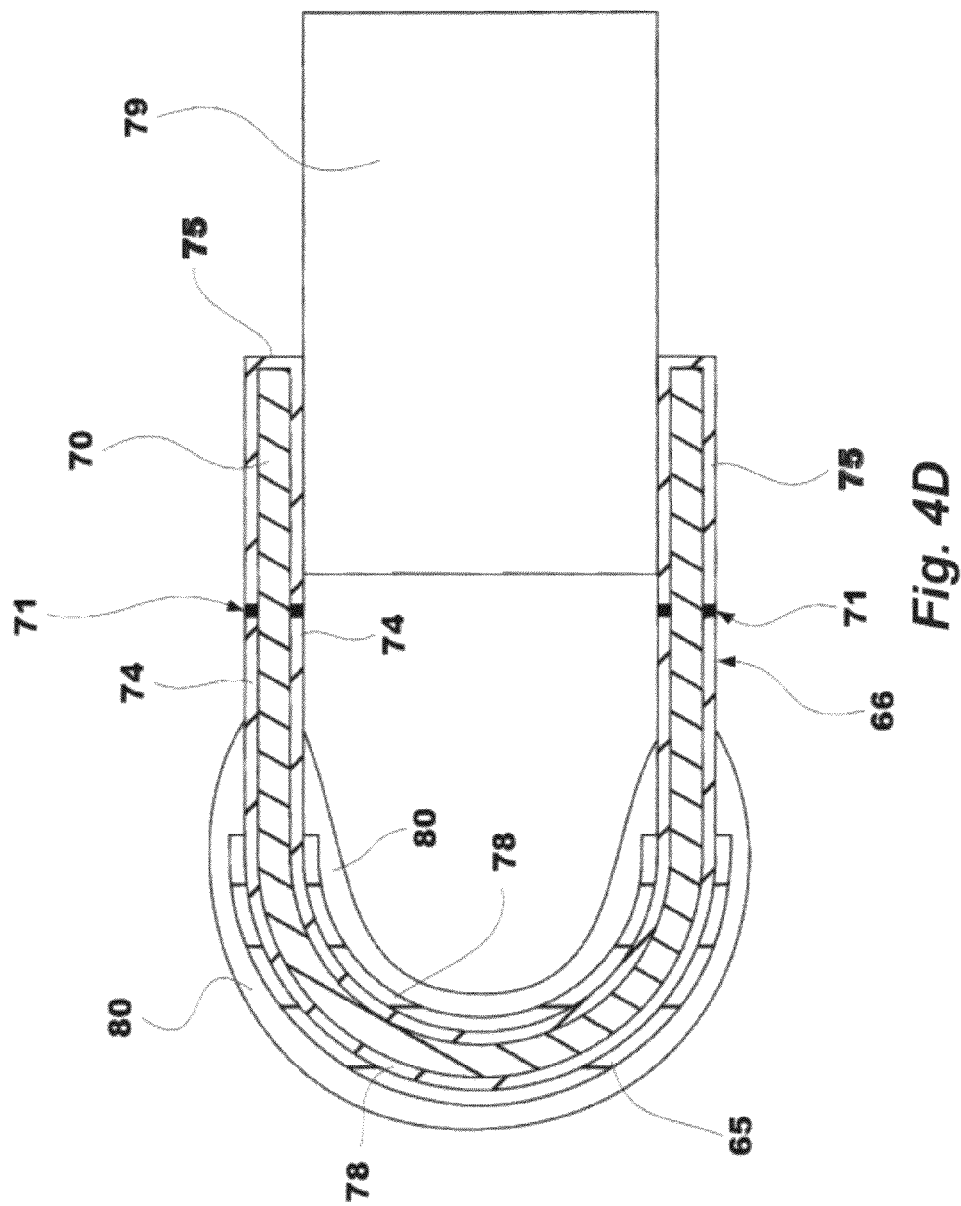
FIG. 4D shows a side cross-sectional view of a portion of a thermal surgical tool system according to principles of the present invention.

Alternatively, a sleeve 75 may be disposed on the support 70 to facilitate attachment of the conductor 66 to the printed circuit board 79 as is shown in FIG. 4D. The sleeve 75 may be attached to the support 70, for example by TIG welding the sleeve 75 to the support 70. The sleeve 75 may be disposed on the support 70 such that the sleeve 75 is in contact with or connected to the intervening layer 74, as indicated by location 71, so that electrical energy may be transferred from the sleeve 75 to the intervening layer 74 and thereby cause heating of the ferromagnetic portion 65. Thus, in contrast to the intervening layer 74 shown in FIG. 4C, the intervening layer 74 shown in FIG. 4D does not extend along the entire length of the support.

Figure 5:
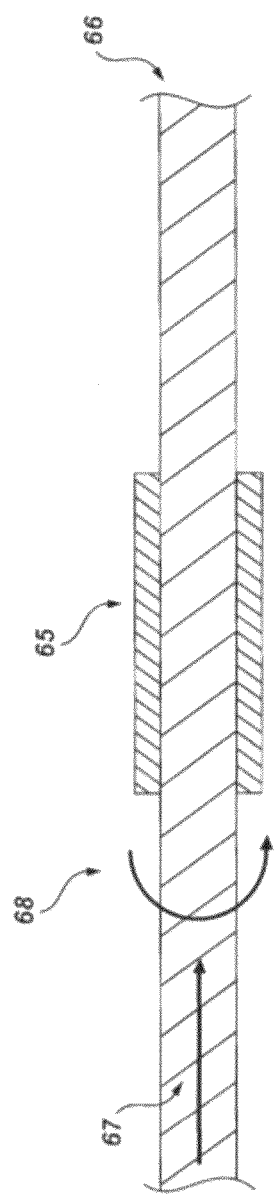
FIG. 5 shows a close-up, side cross-sectional view of a conductor having a single layer of ferromagnetic material disposed thereon in accordance with one aspect of the present invention.

Turning now to FIG. 5, a longitudinal cross section of a conductor having a ferromagnetic material disposed thereon is shown. An alternating current 67 is passed through conductor 66 causing heating in the ferromagnetic material 65. As there is very little mass to the ferromagnetic material 65, the passage of alternating current causes the ferromagnetic material 65 to quickly heat. Similarly, the ferromagnetic coating 65 is small in mass compared to conductor 66 and therefore heat will quickly dissipate therefrom due to thermal transfer from the hot ferromagnetic material 65 to the cooler and larger conductor 66, as well as from the ferromagnetic material 65 to the surrounding environment.

It should be appreciated that while the figures show a solid circular cross-section, the conductor cross-section may have various geometries. For instance, the conductor may be a hollow tubing such that it reduces thermal mass. Whether solid or hollow, the conductor may also be shaped such that it has an oval, triangular, square or rectangular cross-section.

As is also evident from FIG. 5, the ferromagnetic coating may be between a first section (or proximal portion) and a second section (or distal portion) of the conductor. This may provide the advantage of limiting the active heating to an area smaller than the entire conductor. A power supply may also connect to the first and second section to include the ferromagnetic material within a circuit providing power.

A method of making the surgical instrument may include the steps of: selecting a conductor and plating a ferromagnetic material upon the conductor, such that passage of electrical energy through the conductor causes substantially uniform ferromagnetic heating of the ferromagnetic material, wherein the ferromagnetic heating is sufficient to produce a desired therapeutic tissue effect.

Optional steps to the method may include: selecting a size of a conductor having a ferromagnetic material disposed on a portion thereof according to a desired procedure; selecting a thermal mass of a conductor having a ferromagnetic material disposed on a portion thereof according to a desired procedure; selecting a conductor from the group of loop, solid loop, square, pointed, hook and angled; configuring the oscillating electrical signal to heat the ferromagnetic material to between 37 and 600 degrees Centigrade; configuring the oscillating electrical signal to heat the ferromagnetic material to between 40 and 500 degrees Centigrade; causing the ferromagnetic material to heat to between about 58-62 degrees Centigrade to cause vascular endothelial welding; causing the ferromagnetic material to heat to between about 70-80 degrees Centigrade to promote tissue hemostasis; causing the ferromagnetic material to heat to between about 80-200 degrees Centigrade to promote tissue searing and sealing; causing the ferromagnetic material to heat to between about 200-400 degrees Centigrade to create tissue incisions; or causing the ferromagnetic material to heat to between about 400-500 degrees Centigrade to cause tissue ablation and vaporization. Treatment may include incising tissue, causing hemostasis, ablating tissue, or vascular endothelial welding.

Figure 6:
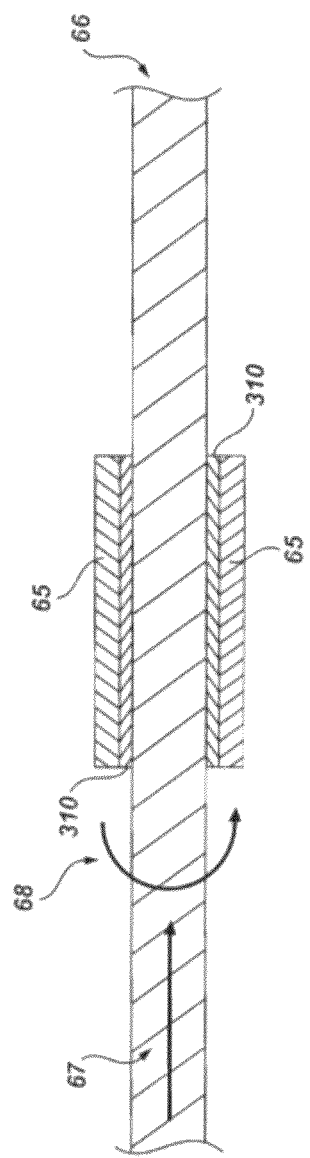
FIG. 6 shows a close-up, side cross-sectional view of a conductor with a thermal insulator and ferromagnetic material in accordance with one aspect of the present invention.

Turning now to FIG. 6, a close-up, longitudinal cross-sectional view of a single layer cutting tip with a thermal insulator 310 is shown. A layer of thermal insulator 310 may be placed between the ferromagnetic material 65 and the conductor 66. Putting a layer of thermal insulator 310 may aid in the quick heating and cool-down (also known as thermal response time) of the instrument by reducing the thermal mass by limiting the heat transfer to the conductor 66.

The thickness and composition of the thermal insulator may be adjusted to change the power delivery and thermal response time characteristics to a desired application. A thicker layer of thermal insulator 310 may better insulate the conductor 66 from the ferromagnetic coating 65, but may require an increased power compared with a thinner layer of thermal insulator 310 in order to induce a magnetic field sufficient to cause the ferromagnetic material 65 to heat.

In FIGS. 7A-7G a plurality of embodiments are shown in which the surgical tip 210 includes a conductor 66 which has a portion of its length coated or in electrical communication with a relatively thin layer of ferromagnetic material 65. As shown in FIGS. 7A-7G, the ferromagnetic material 65 may be a circumferential coating around a wire conductor 66. When the wire conductor 66 is excited by a high frequency oscillator, the ferromagnetic material 65 will heat through induction or other ferromagnetic heating according to the power delivered. Because of the small thickness of ferromagnetic material 65 and the tuned efficiency of high frequency electrical conduction of the wire at the position of the ferromagnetic material 65, the ferromagnetic material 65 will heat very quickly (i.e. a small fraction of a second) when the current is directed through the wire conductor 66, and cool down quickly (e.g. a fraction of a second) when the current is stopped.

Turning now to FIGS. 7A, 7B, 7C, 7D, 7E, 7F and 7G, surgical tips comprising conductors with ferromagnetic layers 210a, 210b, 210c, 210d, 210e, 210f and 210g are shown. In each of these embodiments, a portion of the conductors 66 are bent and in electrical communication with a ferromagnetic material 65 such that the ferromagnetic material 65 is only exposed to tissue where the desired heating is to occur. FIGS. 7A and 7B are loop shapes that can be used for tissue cutting or excision, depending upon the orientation of the instrument to the tissue. FIG. 7A shows a rounded geometry, while FIG. 7B shows a squared geometry. FIG. 7C shows a pointed geometry for heated tip applications that can be made very small because the process of tissue dissection, ablation, and hemostasis requires only a small contact point. FIG. 7D shows an asymmetric instrument with a loop geometry, where the ferromagnetic material 65 is only disposed on one side of the instrument. FIG. 7E shows a hook geometry where the ferromagnetic material 65 is disposed on the concave portion of the hook. FIG. 7F shows a hook geometry where the ferromagnetic material 65 is disposed on the convex portion of the hook. FIG. 7G shows an angled geometry, which may be used in similar situations as a scalpel. Use of these various geometries of ferromagnetic material 65 upon a conductor 66 may allow the surgical tip to act very precisely when active and to be atraumatic when non-active.

In one representative embodiment, the electrical conductor may have a diameter of 0.01 millimeter to 1 millimeter and preferably 0.125 to 0.5 millimeters. The electrical conductor may be tungsten, copper, other metals and conductive non-metals, or a combination such as two dissimilar metals joined to also form a thermocouple for temperature measurement. The electrical conductor may also be a thin layer of conductor, such as copper, dispersed around a non-metallic rod, fiber or tube, such as glass or high-temperature plastic, and the conductive material, in turn, may have a thin layer of ferromagnetic material disposed thereon. The magnetic film forms a closed magnetic path around the electrically conductive wire or other conductor. The thin magnetic film may have a thickness of about 0.01-50% and preferably about 0.1% to 20% of the cross-sectional diameter of the wire.

It is therefore possible to operate at high frequencies with low alternating current levels to achieve rapid heating. The same minimal thermal mass allows rapid decay of heat into tissue and/or the conductor with cessation of current. The instrument, having low thermal mass, provides a rapid means for temperature regulation across a therapeutic range between about 37 degrees Celsius and 600 degrees Celsius, and preferably between 40 and 500 degrees Celsius.

A material with a Curie point beyond the anticipated therapeutic need may be selected and the temperature can be regulated below the Curie point.

While some tip geometries are shown in FIGS. 7A through 7G, it is anticipated that multiple different geometries may be used in surgical tips made according to principles of the present invention.

Figure 8:
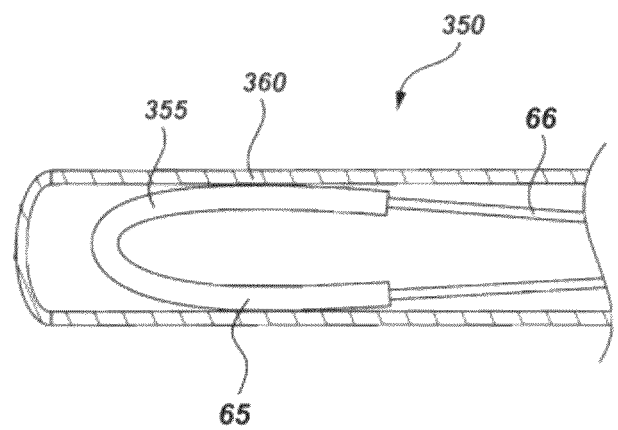
FIG. 8 shows a cut-away view of a retracted snare.

Turning now to FIG. 8, a cut-away view of a snare 350 in a retracted position is shown. A ferromagnetic material is placed on a conductor to form a snare loop 355 and then placed within a sheath 360. While retracted, the snare loop 355 may rest within a sheath 360 (or some other applicator, including a tube, ring or other geometry designed to reduce the width of the snare when retracted). The sheath 360 compresses the snare loop 355 within its hollow body. The sheath 360 may then be inserted into a cavity where the target tissue may be present. Once the sheath 360 reaches the desired location, the snare loop 355 may be extended outside the sheath 360, and end up deployed similar to FIG. 9A. In one embodiment, the conductor 66 may be pushed or pulled to cause extension and retraction of the snare loop 355.

Figure 9A:
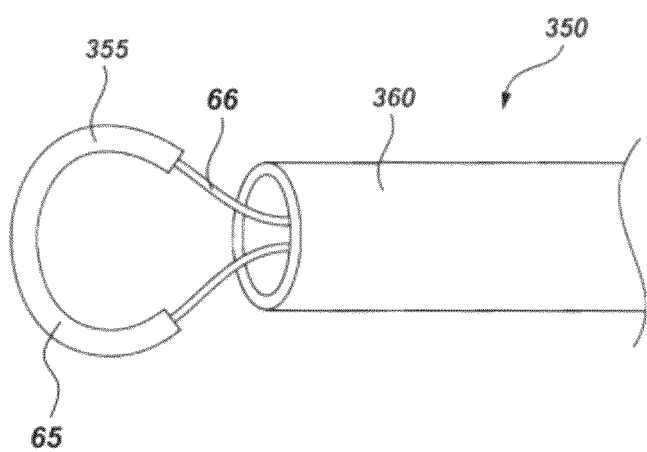
FIG. 9A shows a side view of an extended snare.

Turning now to FIG. 9A, a side view of a snare 350 in an extended position is shown. Once extended, the snare loop 355 may be used in several different ways. In one embodiment, the snare loop 355 may be placed substantially around the target tissue, such that the tissue is within the snare loop 355. The ferromagnetic coating may then be caused to be heated as discussed above. The snare loop 355 is then retracted back into the sheath 360 such that the target tissue is separated and removed from tissue adjacent the target tissue. The desired temperature range or power level may be selected for hemostasis, increased tissue separation effectiveness or other desired setting. For example, the snare 350 may be configured for nasal cavity polyp removal.

In another use, the snare 350 may be configured for tissue destruction. Once within the desired cavity, the snare may be extended such that a portion of the snare loop 355 touches the target tissue. The snare loop 355 may then be heated such that a desired tissue effect occurs. For example, the sheath may be placed near or in the heart and the snare loop 355 heated to cause an interruption of abnormal areas of conduction in the heart, such as in atrial ablation.

Figure 9B:
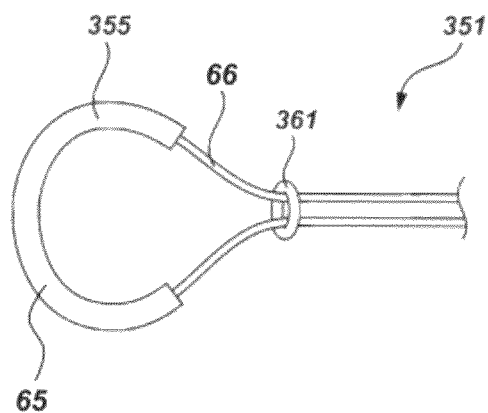
FIG. 9B shows an alternate embodiment of an extended snare.

Turning now to FIG. 9B, an alternate embodiment of a snare 351 is shown. The applicator may be a ring 361 instead of a sheath as in FIG. 9A. Similar to the sheath, the ring 361 may be used to force the loop into an elongated position. Various devices could be used to hold the ring in place during use.

A method of separating tissue may include the steps of: selecting a conductor having a ferromagnetic material disposed on a portion thereof; placing the portion of the conductor having the ferromagnetic material within a tube; inserting the tube into a cavity; deploying the portion of the conductor having the ferromagnetic material within the cavity; and delivering an oscillating electrical signal to the conductor so as to heat the ferromagnetic material while the heated ferromagnetic material is in contact with a target tissue.

Optional steps may include: the deploying step further comprises placing the ferromagnetic material substantially around the target tissue; retracting the ferromagnetic material portion of the conductor into the tube; causing hemostasis in the target tissue; forming the conductor into a bent geometry such that a portion of the conductor remains within the tube; and touching a ferromagnetic covered portion of the bent geometry to the target tissue.

A method of removing tissue may include the steps of: selecting a conductor having at least one portion having a ferromagnetic conductor disposed thereon; and placing the ferromagnetic conductor around at least a portion of the tissue and pulling the ferromagnetic conductor into contact with the tissue so that the ferromagnetic conductor cuts the tissue.

Optional steps may include: using a conductor having a plurality of ferromagnetic conductors in an array or passing an oscillating electrical signal through the conductor while the ferromagnetic material is in contact with the tissue.

Figure 10A:
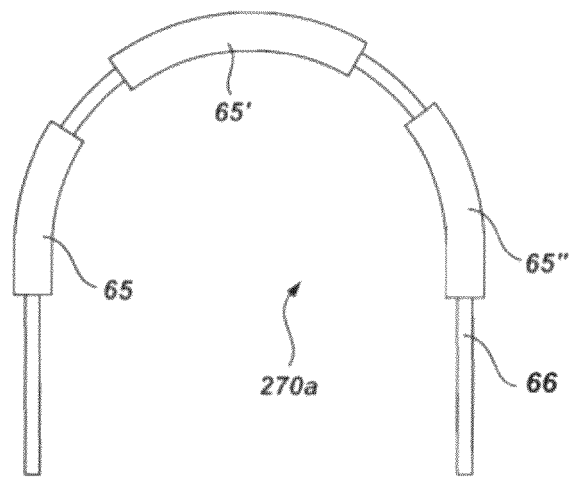
FIG. 10A shows a close-up view of a ferromagnetic conductor surgical instrument with a loop geometry and linear array of ferromagnetic segments.

Turning now to FIG. 10A, a close-up view of a cutting tip with a loop geometry and linear array of coatings is shown. According to one aspect of the invention, there may be more than one layer of ferromagnetic material separated by gaps along the length of a single conductor. This is termed a linear array of ferromagnetic elements.

Figure 10B:
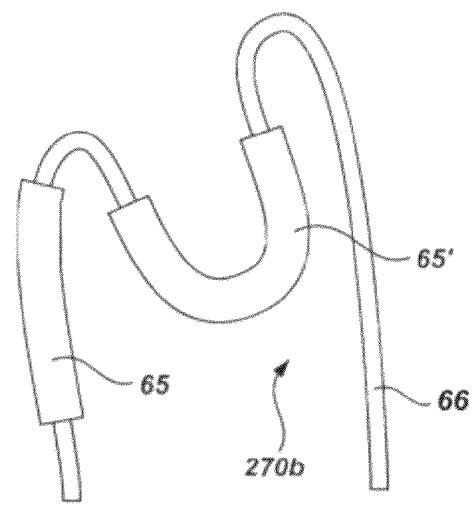
FIG. 10B shows a close up view of a ferromagnetic conductor surgical instrument with an alternate hook geometry and linear array.

According to one aspect, a loop geometry 270a may have multiple ferromagnetic layers 65, 65', and 65" which are separated by gaps on a conductor 66. In another embodiment shown in FIG. 10B, a close up view of a cutting tip with an alternate hook geometry 270b and linear array of ferromagnetic coatings 65 and 65' is shown on a conductor 66. The linear array may include the advantage of allowing flexibility in building a desired thermal geometry.

The conductor 66 which may be formed of an alloy having shape memory, such as Nitinol (nickel titanium alloy). A Nitinol or other shape memory alloy conductor can be bent into one shape at one temperature, and then return to its original shape when heated above its transformation temperature. Thus, a physician could deform it for a particular use at a lower temperature and then use the ferromagnetic coating to heat the conductor to return it to its original configuration. For example, a shape memory alloy conductor could be used to form a snare which changes shape when heated. Likewise, a serpentine shape conductor can be made of Nitinol or other shape memory alloy to have one shape during use at a given temperature and a second shape at a higher temperature. Another example would be for a conductor which would change shape when heated to expel itself from a catheter or endoscope, and then enable retraction when cooled.

In another embodiment, the ferromagnetic layers may be formed in such a way that an individual layer among the linear array may receive more power by tuning the oscillating electrical energy. The tuning may be accomplished by adjusting the frequency and/or load matching performed by the power source to specific ferromagnetic layers.

Figure 11:
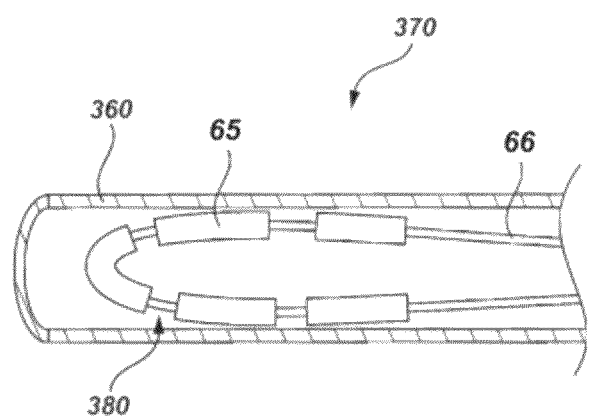
FIG. 11 shows a cut-away view of a retracted snare with an array of ferromagnetic segments.

Turning now to FIG. 11, a cut-away view of a snare instrument 370 with a linear array of ferromagnetic layers in a retracted position is shown. Some ferromagnetic materials may lack the elasticity to effectively bend into a retracted position. Therefore, individual segments 65 may be separated by gaps 380 such that the conductor 66 may be flexed while the ferromagnetic segments 66 may remain rigid.

Figure 12:
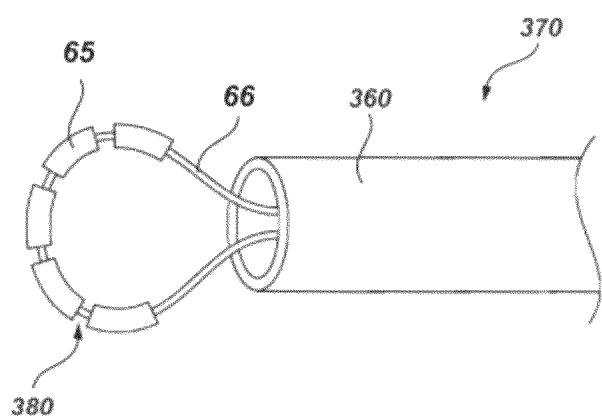
FIG. 12 shows a side view of an extended snare with a linear array of ferromagnetic segments.

Similarly, the snare instrument 370 may be extended, as seen in FIG. 12. The gaps 380 between the ferromagnetic segments 65 may be adjusted such that the heating effect will be similar in the gaps 380 as the coating segments. Thus, the snare instrument 370 with linear array may act similar to the snare with a single, flexible ferromagnetic layer shown in FIGS. 8 and 9.

Figure 13A:
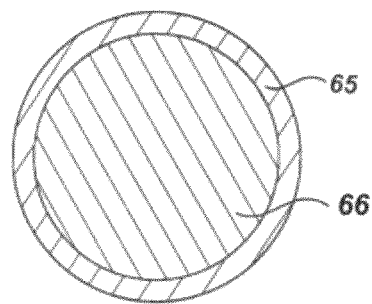
FIG. 13A shows an axial cross-sectional view of a single layer ferromagnetic conductor in the ferromagnetic heating region.

Turning now to FIG. 13A, a cross-sectional view of a single layer cutting tip in the ferromagnetic heating region is shown. The ferromagnetic material 65 is disposed over a conductor 66. The ferromagnetic coating 65 provides several advantages. First, the ferromagnetic coating 65 is less fragile when subjected to thermal stress than ferrite beads, which have a tendency to crack when heated and then immersed in liquid. The ferromagnetic conductor has been observed to survive repeated liquid immersion without damage. Further, the ferromagnetic material 65 has a quick heating and quick cooling quality. This is likely because of the small amount of ferromagnetic material 65 that is acted upon by the alternating current, such that the power is concentrated over a small area. The quick cooling is likely because of the small amount of thermal mass that is active during the heating. Also, the composition of the ferromagnetic material 65 may be altered to achieve a different Curie temperature, which may provide a broader thermal operating range below the Curie temperature.

Figure 13B:
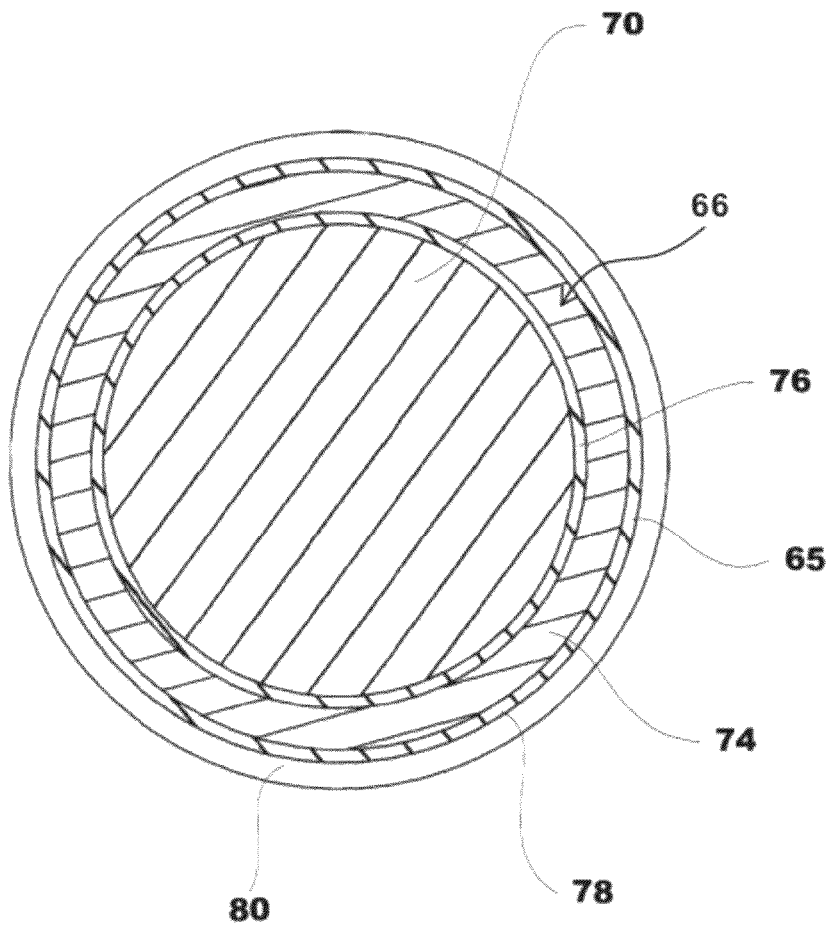
FIG. 13B shows an axial cross-sectional view another ferromagnetic conductor in the ferromagnetic heating region according to principles of the present invention.

The ferromagnetic material 65 can be used to contact the tissue directly, or, a non-stick coating, such as TEFLON (PTFE), or similar material, could be applied over the ferromagnetic coating and conductor to prevent sticking to the tissue (as shown in FIG. 13B). Alternatively, the ferromagnetic material could be covered with another material, such as gold, to improve biocompatibility, and/or polished, to reduce drag force when drawing through tissue. The ferromagnetic material 65 could also be covered by a thermally-conductive material to improve heat transfer. In fact, single or multi-layered coatings beneath the ferromagnetic material or on top of the ferromagnetic material may be selected to have multiple desirable properties as discussed in more detail below.

Turning now to FIG. 13B, a cross-sectional view of a surgical tip in the ferromagnetic-portion is shown. The ferromagnetic portion 65 may be disposed circumferentially about a conductor 66. The surgical tip may be constructed of multiple layers. Each of the multiple layers may comprise a different material, or combinations of the same or different materials, so as to take advantage of the different properties of the various materials when used as a surgical tip. For example, the conductor 66 may include a support 70 which may be comprised of a material having a high Young's modulus, i.e. strength to resist bending. The conductor 66 may also include an the intervening layer 76, which may be a strike layer to facilitate attachment of additional layers, and an intervening layer 74, which may comprise one or more layers of copper, silver, or other material which is highly conductive. The ferromagnetic material 65, which may be a thin layer or coating 78 is then attached to the intervening layer 74 and a biocompatible material 80 may be disposed over substantially all or a portion of the length of the conductor 66. A method for tissue destruction may include the steps of selecting a conductor having a ferromagnetic material disposed on a portion thereof; and delivering an oscillating electrical signal to the conductor so as to heat the ferromagnetic material and destroy tissue.

Optional steps of the method may include monitoring the tissue and ceasing delivery of the oscillating electrical signal to the conductor when the desired tissue destruction has occurred or undesired tissue effects are to be prevented.

Optional steps of the method may include providing electrical connections on the conductor configured for receiving oscillating electrical energy.

Figure 14:
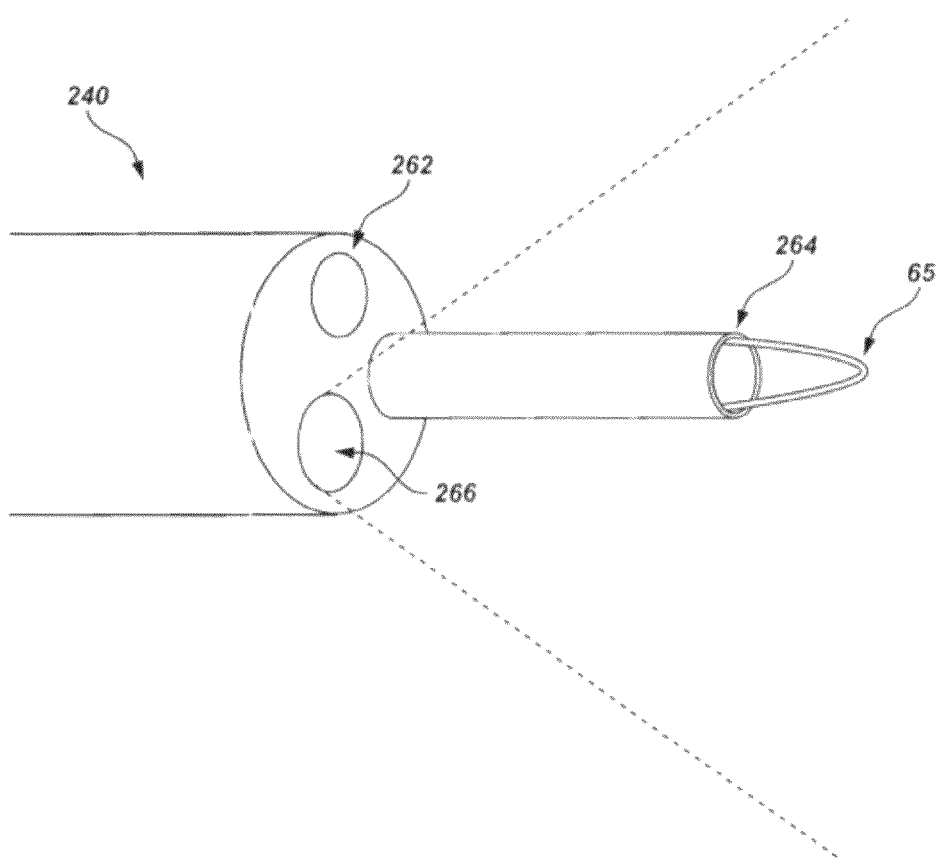
FIG. 14 shows an alternate embodiment of a ferromagnetic conductor surgical instrument having a ferromagnetic loop tip disposed within an endoscope.

Turning now to FIG. 14, an endoscope 240 with a viewing channel 262 of rod lens type or organized fiber bundle type aside a light emitting source 266 is shown. A loop coagulator/cutter 264 is shown which comprises the ferromagnetic conductor 65. Such an adaptation is contemplated in snare applications such as colon polypectomy or sealing and cutting applications in various laparoscopic procedures. Other sensing modalities include near field tumor cell detection or infrared heat monitoring. Instrument configurations similar to the described endoscope 240 can be embodied in instruments that can be delivered to target tissue through the lumen of a catheter.

According to one aspect, tumor cells are caused to be tagged with materials that fluoresce when exposed to ultraviolet light. The endoscope 240 may contain a light source 266, and sensor or optics within the channel 262 that return the detected florescence. The ferromagnetic material 65 portion of the endoscope 240 may then be directed at the tagged tissue for destruction.

According to another aspect, materials are deposited around target tissue or bone in a solidified condition. Once delivered, the materials are melted to conformation at the site by activation by the endoscope 240 described above. Examples of use of this embodiment include fallopian tube sealing and osteosynthesis. Furthermore, such materials could be removed by melting with the same or similar endoscope 240, and aspirated through a central lumen of the endoscope 240. In yet further applications, materials may be delivered in liquid form, and cured by a thermal heating process induced by the endoscope 240.

Alternatively, the conductor may be part of a bundle of fibers. The fibers may be contained within a catheter or otherwise bundled together. The conductor may have a ferromagnetic layer, while the other fibers may have other purposes that include visual observation, sensing, aspiration, or irrigation.

A method of tissue ablation may include the steps of: selecting a catheter with a ferromagnetic covered conductor; causing the ferromagnetic covered conductor to touch tissue to be ablated; and delivering power to the ferromagnetic covered conductor.

Optional steps may include: directing the catheter to the tissue through the aid of an endoscope; selecting a ferromagnetic conductor disposed on the catheter; selecting a ferromagnetic conductor contained within the catheter; causing the ferromagnetic conductor to be deployed from the catheter; or touching the ferromagnetic conductor to the tissue to be ablated.

A method of delivering a substance into a body may include the steps of: selecting a catheter with a ferromagnetic conductor; placing a substance in the catheter; inserting the catheter into a body; and causing power to be sent to the ferromagnetic conductor.

Optional steps may include: selecting a substance for osteosynthesis; selecting a substance for fallopian tube sealing; or melting the substance in the catheter.

A method of treating tissue may include the steps of: selecting a catheter with a ferromagnetic conductor; placing the catheter in contact with tissue; and selecting a power setting. The temperature range may correspond to a temperature range or desired tissue effect. The desired tissue effect may be selected from the group of vascular endothelial welding, hemostasis, searing, sealing, incision, ablation, or vaporization. In fact, the power setting may correspond to a desired tissue effect.

Figure 15:
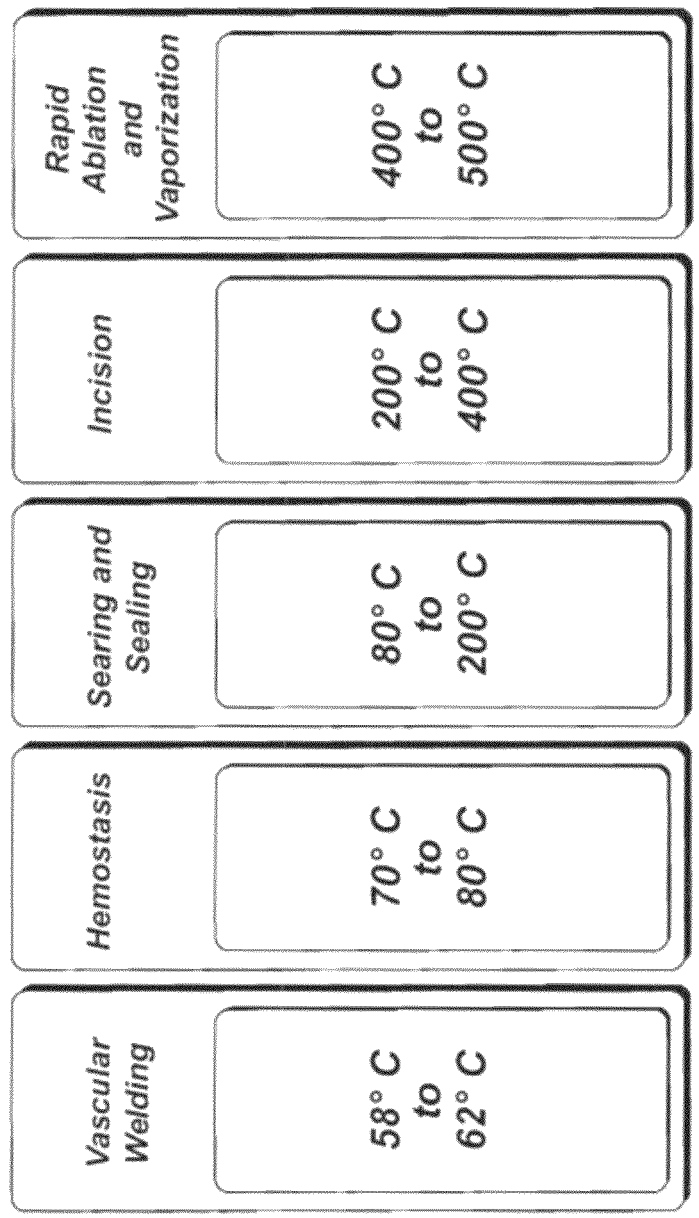
FIG. 15 shows a thermal spectrum as related to tissue effects.

Turning now to FIG. 15, a temperature spectrum is disclosed. Tissue may react differently at different temperatures with a tissue treatment element (such as a ferromagnetic conductor) and thus temperature ranges will result in different treatments for tissue. Specific tissue treatments are somewhat variable due to inconsistencies including tissue type and patient differences. The following temperatures have been found to be useful. Vascular endothelial welding may be optimal at 58-62 degrees Centigrade. Tissue hemostasis without sticking may be achieved at 70-80 degrees Centigrade. At higher temperatures, tissue searing and sealing may occur more quickly, but coagulum may build-up on the instrument. Tissue incision may be achieved at 200 degrees Centigrade with some drag due to tissue adhesion at the edges. Tissue ablation and vaporization may occur rapidly in the 400-500 degree Centigrade range. Thus, by controlling the temperature the "treatment" of tissue which the device delivers can be controlled, be it vascular endothelial welding, tissue incision, hemostasis or tissue ablation.

Besides the advantages of uses in tissue, the surgical instrument may also be self-cleaning. In one embodiment, when activated in air, the instrument may achieve a temperature sufficient to carbonize or vaporize tissue debris.

According to the spectrum disclosed above, power delivery settings corresponding to the desired temperature range may be included in the power delivery switch. In one embodiment, the foot pedal may have several stops that indicate to the surgeon the likely tip temperature range of the current setting.

Turning now to FIGS. 16 to 18C, a thermal resecting instrument is shown. A thermal resecting instrument may allow a surgeon to separate and scoop tissue while providing the benefits of hemostasis. To this end, the conductor may be shaped to enclose or substantially enclose a void through which cut tissue will pass. It will be appreciated that the shape of the conductor 66 may be arc-shaped, similar to that shown in FIG. 7A, loop-shaped similar to that shown in FIGS. 9A and 9B, oblong similar to that shown in FIG. 8 or FIG. 18D, squared or squared-off similar to that shown in FIG. 7B, angular or pointed similar to that shown in FIG. 7C or any other shape which can be used for tissue resecting. The drawings show the conductor as being generally loop shaped but should be considered to show the other shapes as well. Additionally, it will be appreciated that the ferromagnetic material may cover and extend along the conductor for various lengths depending on the desired use.

As mentioned with respect to FIGS. 7A and 7B, a shaped ferromagnetic conductor can be used both for cutting and excising tissue. When held in one orientation, the outer surface of the shaped ferromagnetic conductor will cut like a knife. When rotated 90 degrees or some other angle, the cutting element can cut out tissue, either by cutting off tissue (i.e. a polyp) or scooping out tissue (i.e. a tumor) without substantially changing the orientation of the handle.

Figure 16:
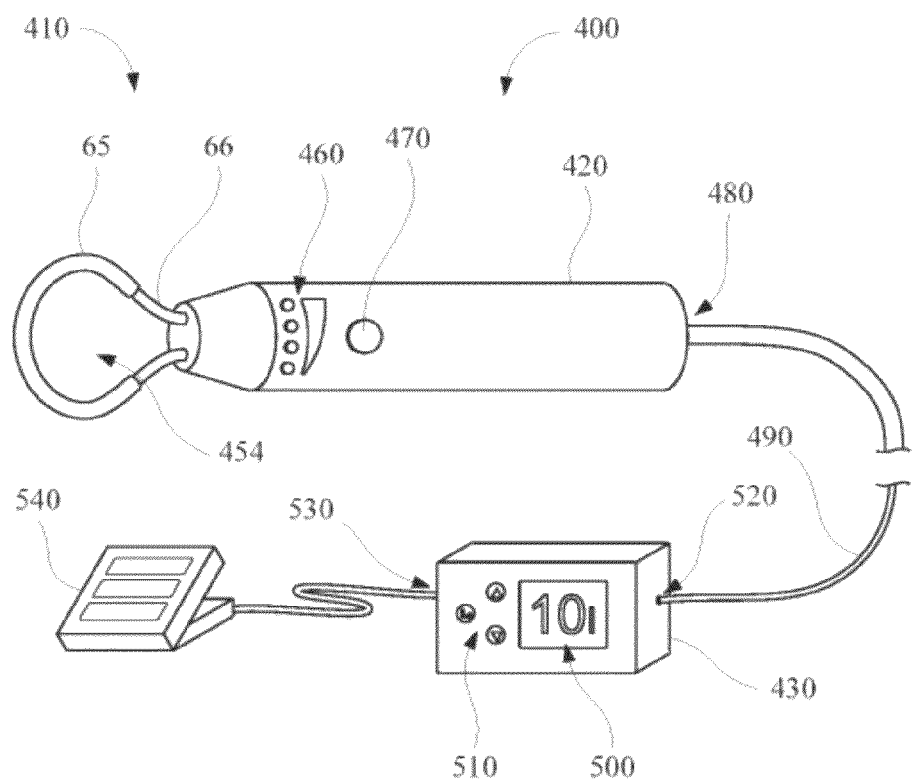
FIG. 16 shows a thermal resecting instrument and system.

Turning now to FIG. 16, a thermal resecting instrument 400 and system 410 is shown. The thermal resecting instrument system 410 may include a handpiece 420 and power supply 430. The power supply 430 may supply power and receive control input from the handpiece 420.

The handpiece 420 may include an arc-shaped or loop-shaped conductor 66 having a ferromagnetic layer 65 disposed about a void 454, power display 460, push button control 470 and supply terminals 480 for receiving a cable 490. Power directed to the conductor 66 may cause the ferromagnetic layer 65 to heat. The power display may receive information from the power supply 430 and display current information, such as the current power setting. Push button control 470 may send information to the power supply 430, such as directing the power supply to start supplying power or turn off power depending on the current state of power. The handpiece 420 may also be removably attached to the cable 490 through supply terminals 480.

The power supply 430 may include a signal generator, display 500, controls 510, handpiece terminals 520, control terminals 530 and remote control functionality, such as a foot pedal 540. The signal generator may prepare a waveform to be sent to the handpiece 420. The display 500 may be used with the controls 510 to view and edit settings, including power level, waveform, and tip configuration. Handpiece terminals may be used to connect the handpiece 420 to the power supply through one or more cables 490, including delivering power, suction, insufflation, etc. Control terminals 530 may allow connection of external controls, such as a foot pedal 540. The external controls may be used to alter settings, such as power level, suction power, airflow or irrigation.

In one embodiment, a surgeon may preset the device to specific settings, including power levels and waveforms. The surgeon may then select a tip or handpiece with the desired loop configuration, such as size, diameter, angle and thickness, and connect the handpiece to the power supply 430 through handpiece terminals 520. The surgeon may control the handpiece power levels and other options through the use of handpiece controls, such as push button control 470 and foot pedal 540. When the desired setting is achieved, the surgeon may scoop tissue by placing the ferromagnetic coating against the tissue and pushing or pulling the handpiece to drive the handpiece into the tissue and then out again. Optionally, a surgeon may also save frequently used settings as "favorites."

Figure 17:
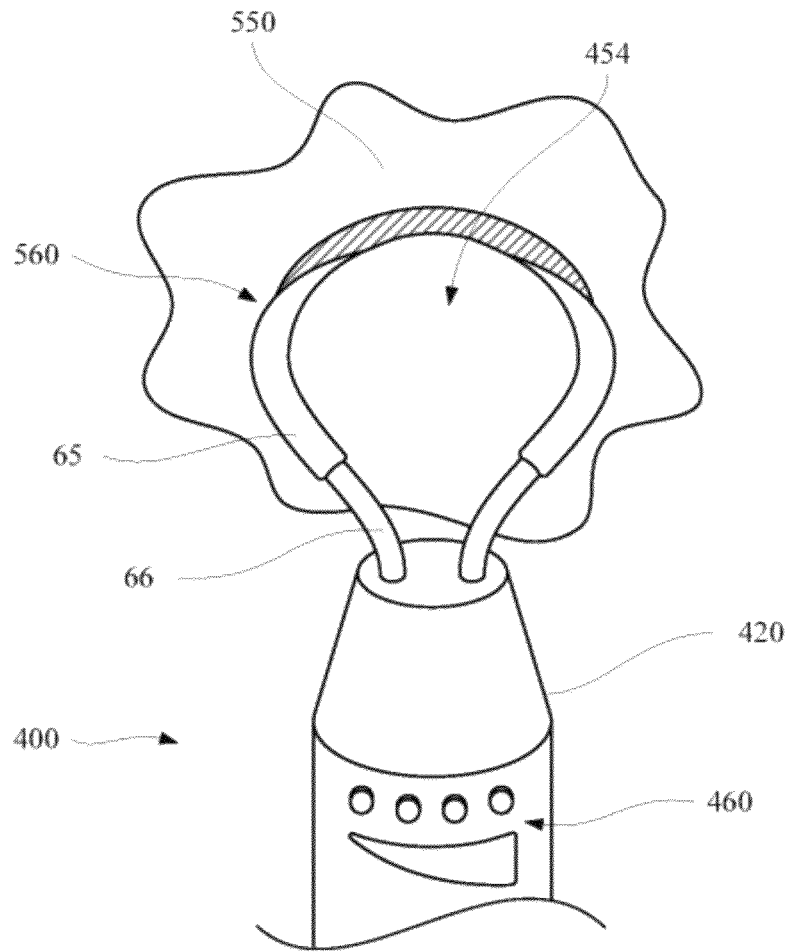
FIG. 17 shows a thermal resecting instrument resecting a piece of tissue, such as a tumor.
Figure 17A:
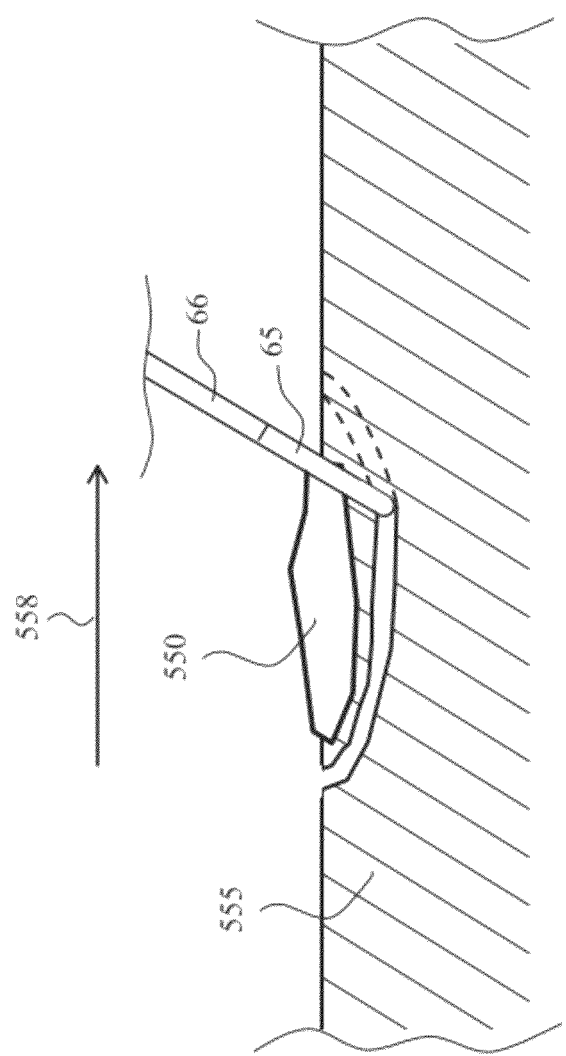
FIG. 17A shows a side, cross-sectional view of a thermal resecting instrument resecting a piece of tissue.

FIGS. 17 and 17A show a thermal resecting instrument 400 resecting a tumor 550. A ferromagnetic covered conductive loop 560 forming a ferromagnetic region and defining a void 454 for receiving tissue, so that the loop 560 may be used to scoop larger or smaller amounts of tissue, such as tumor 550. Larger amounts of tissue may be removed by causing the loop 560 to enter deeper into the tissue. Smaller amounts of tissue may be removed by causing the loop 560 to enter more shallowly or by scraping the surface. In either, case, the loop 560 may resect tissue with a single motion. In other words, the loop 560 may be disposed at an angle relative to the path of travel (indicated by arrow 558 in FIG. 17A) and be advanced below a surface level of the tumor 550 or other tissue being resected (as more clearly shown in FIG. 17A) to thereby leave a three dimensional void in the tumor 550 or other tissue while simultaneously cauterizing the tissue so as to stop bleeding, etc. Thus, the loop 560 could scoop out a portion of tissue and thereby remove a tumor 550 or other growth and seal the wound with a single pass. Likewise, the loop 560 can be used to remove undesirable tissue, etc., one scoop or pass at a time with each pass leaving the tissue sealed. Such may allow a surgeon, for example, to repeatedly advance through a tumor or other tissue which is desired to be removed, and then observe with each pass whether all of the undesirable tissue has been moved.

By rotating the angle of the loop 560, the surgeon can control the cross-sectional area of the three dimensional void or channel left once the undesirable tissue has been removed. For example, a surgeon could rotate the loop 560 and insert the loop 550 into the tissue at a 45 degree angle to the path of travel 558, for example, to cut a void having a first width, and then rotate the loop to be generally perpendicular to the zone of the travel 558 to resect a wider portion of tissue. Thus, the surgeon can adjust the position of the loop to minimize or maximize the amount of tissue at any particular location being taken out with a single pass.

Contrasted with a blade (and even many electrosurgical devices), the blade may require several cuts and/or a more complex circular motion to remove tissue. Thus, the loop 560 provides the advantage of a single motion to resect tissue three dimensionally with the advantages of removing smaller or larger portions of tissue with hemostasis.

Alternatively, the loop 560 may be rotated so that an outer surface (e.g. a surface of the loop opposite the void 454) can be used to incise tissue. Thus, the loop 560 can be used as either, or both, a resecting instrument by surrounding tissue such that the tissue is located within the void 454 and drawing the loop 560 through the tissue, or more like a traditional blade or scalpel to incise tissue.

Resecting tumors with the thermal resecting instrument 400 may provide several benefits. As some tumors promote angiogenisis (increase blood vessel formation) they may have increased blood flow. Thus, hemostasis may become more important as the surgeon is able to cut and seal simultaneously. As the thermal resecting instrument 400 may resect tissue while providing hemostasis on the tissue remaining, bleeding may be reduced. Reduced bleeding may provide a clearer operating site and reduce patient blood loss.

Figures 18A, 18B:
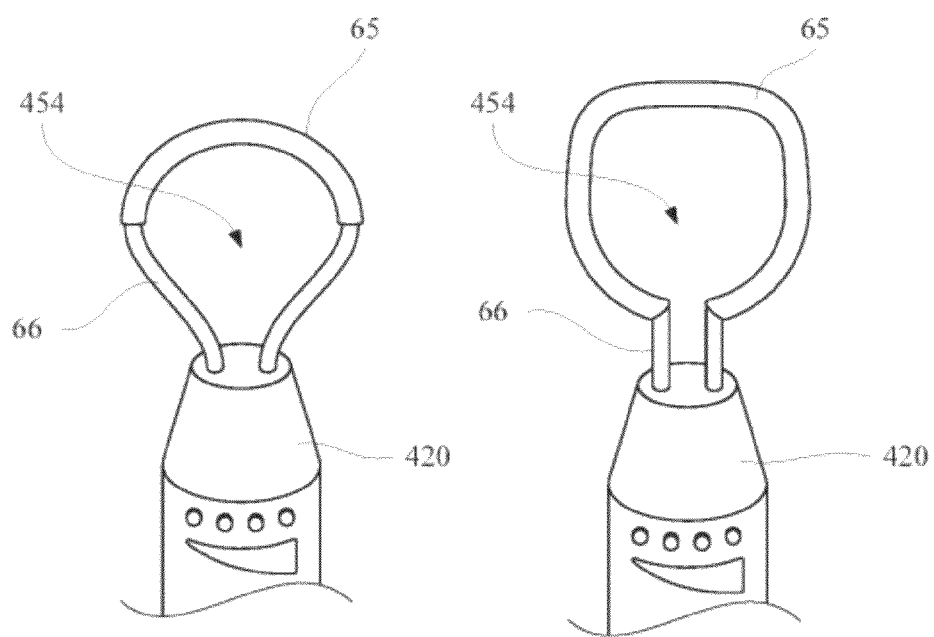
FIG. 18A shows a thermal resecting instrument with an arc or loop which is covered with ferromagnetic material in a semi-circle.
FIG. 18B shows a thermal resecting instrument with an arc which is covered with ferromagnetic material in nearly a complete circle.
Figures 18C, 18D:
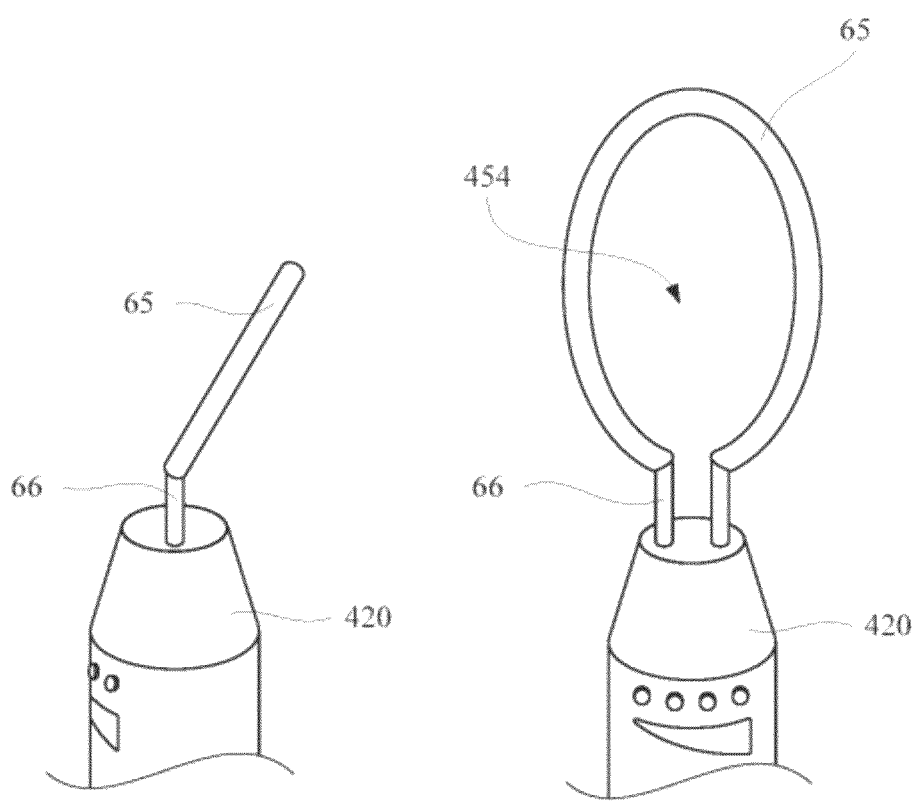
FIG. 18C shows a side view of a thermal resecting instrument with a cutting element disposed at an angle such that the cutting element is oriented in a non-parallel position with respect to the handpiece.
FIG. 18D shows an oblong thermal resecting instrument.

A ferromagnetic covered conductive loop 560 may be produced in a variety of shapes, diameters, sizes, thicknesses and other configurations adapted to the needs of the surgeon. For example, FIGS. 18A-18D show exemplary ferromagnetic covered conductive loops having ferromagnetic regions. FIG. 18A shows a thermal resecting instrument with a semi-circular ferromagnetic region; FIG. 18B shows a thermal resecting instrument with a near circular ferromagnetic region; FIG. 18C shows a side view of a thermal resecting instrument with a cutting element disposed at an angle such that the cutting element is oriented in a non-parallel position with respect to the handpiece 420; and FIG. 18D shows an oblong thermal resecting instrument.

The shape of the arc may determine the depth versus volume of tissue removed. Comparing FIG. 18B with FIG. 18D, the rounded shape of FIG. 18B may remove more tissue across a greater diameter. The oblong shape of 18D may allow a more targeted, but deeper removal of tissue.

The size of the conductor 66, shape of the conductor 66, and area covered by the ferromagnetic layer 65 disposed along the conductor 66, may also affect the amount of tissue removed. The semi-circular arc of FIG. 18A may be used to remove tissue at a more shallow depth than the full arc of FIG. 18B, without the creation of excessive heat.

An angle of the cutting element, as seen in FIG. 18C, may aid in surgery. For example, the angle of the cutting element may allow better access to tissue within confined spaces. It may also provide a better view of the surgical site because the cutting element is off of the center axis of the handpiece.

It will be appreciated that the thermal surgical instrument system in accordance with the present invention will have a wide variety of uses. Not only can it be used on humans, it can also be used to cut tissue of other animals, such as in the context of a veterinarian or simply cutting tissues or biomaterials, such as those used for implantation, into smaller pieces for other uses.

Certain embodiments of the surgical system may have broad application within surgery as well. A loop geometry may have advantages in cutting, coagulation and biopsy applications. A blade geometry may have advantages for cutting and hemostasis applications. The point geometry may have advantages in dissection and coagulation applications, and in particular, neurodissection and coagulation. However, the application of a geometry may be further configured and tailored to an application by diameter, length, material characteristics and other characteristics discussed above.

While the present invention has been described principally in the area of surgical instruments and the treatment of live tissue (though it can be used on dead tissue as well), it will be understood that an instrument made in accordance with the present invention and the methods discussed herein may have other uses. For example, a cutting instrument could be formed for butchering meat. Whether the meat is fresh or frozen, the instrument can be useful. For example, a cutting blade which is heated to a high temperature will cut through frozen meat. However, when power is no longer supplied, the "cutting" edge is safe to the touch. Likewise, cutting meat with a hemostasis setting would slightly sear the exterior of the meat, locking in juices. Other uses of the instruments discussed herein will be understood by those skilled in the art in light of the present description.

There is thus disclosed an improved thermally adjustable surgical instrument. It will be appreciated that numerous changes may be made to the present invention without departing from the scope of the claims.

What is claimed is:

1. A thermal resecting instrument comprising:
    a thermal resecting element comprising:
        a conductor loop defining a void for receiving tissue and
        a ferromagnetic layer coating and in electrically conductive communication with a surface of at least a portion of the conductor loop, the ferromagnetic layer forming a ferromagnetic region disposed along the conductor loop, the conductor loop extending from a position prior to the ferromagnetic layer, through the ferromagnetic region and to a position beyond the ferromagnetic layer;
    wherein the thermal resecting element is configured to allow passage of electrical energy from a conductor loop location prior to the ferromagnetic region to a conductor loop location beyond the ferromagnetic region, to thereby cause the ferromagnetic layer to heat, and
    wherein the ferromagnetic layer has a thickness of between about 1 μm and about 50 μm.

2. The thermal resecting instrument of claim 1, wherein the ferromagnetic region extends along the conductor loop so as to form a generally semi-circular ferromagnetic region.

3. The thermal resecting instrument of claim 1, wherein the ferromagnetic region extends along substantially all of the conductor loop.

4. The thermal resecting instrument of claim 1, wherein the conductor loop comprises a material having a Young's Modulus of at least 118 GPa.

5. The thermal resecting instrument of claim 1, wherein the conductor loop comprises a material having a Young's Modulus of at least about 400 GPa.

6. The thermal resecting instrument of claim 1, wherein the conductor loop further comprises a support extending across substantially all of the conductor loop.

7. The thermal resecting instrument of claim 6, wherein the conductor loop further comprises at least one intervening layer disposed between the support and the ferromagnetic layer.

8. The thermal resecting instrument of claim 1, further comprising a body, wherein the thermal resecting element is connected to the body and disposed at an angle such that the thermal resecting element is oriented in a non-parallel position with respect to the body.

9. The thermal resecting instrument of claim 1, wherein the ferromagnetic layer has a thickness of between about 2 μm and about 30 μm.

10. The thermal resecting instrument of claim 1, wherein the ferromagnetic layer has a thickness of between about 2 μm and about 10 μm.

11. The thermal resecting instrument of claim 1, wherein the ferromagnetic layer has a thickness sufficient to prevent fracturing of the ferromagnetic layer when subjected to thermal stress passing from a first medium to a second medium.

12. A thermal resecting system comprising:
a handpiece;
a continuous conductor having a first end and a second end and defining a void through which tissue can pass;
a ferromagnetic layer coating and in electrically conductive communication with a surface of at least a portion of the continuous conductor between the first end and the second end; and
electrical leads attached to the first end and the second end of the continuous conductor for supplying electrical energy to the continuous conductor; and
a power supply in communication with the electrical leads for providing the electrical energy to the continuous conductor; and
wherein the ferromagnetic layer has a thickness of between about 1 μm and about 50 μm.

13. The thermal resecting system of claim 12, wherein the thermal resecting system is configured to allow passage of the electrical energy at a predetermined frequency through the continuous conductor and the ferromagnetic layer, to thereby cause direct heating of the ferromagnetic layer sufficient to treat the tissue.

14. The thermal resecting system of claim 13, wherein the continuous conductor has a generally loop-shaped portion and wherein the ferromagnetic layer covers about half of the loop-shaped portion.

15. The thermal resecting system claim 13, wherein the continuous conductor has a generally loop-shaped portion that is substantially covered by the ferromagnetic layer.

16. The thermal resecting system of claim 13, wherein the heating of the ferromagnetic layer is substantially uniform.

17. The thermal resecting system of claim 12, wherein the ferromagnetic layer has a thickness of between about 2 μm and about 30 μm.

18. The thermal resecting system of claim 12, wherein the ferromagnetic layer has a thickness of between about 2 μm and about 10 μm.

19. The thermal resecting system of claim 12, wherein the ferromagnetic layer has a thickness sufficient to prevent fracturing of the ferromagnetic layer when subjected to thermal stress passing from a first medium to a second medium.

20. A surgical tip having a continuous conductor having a first end and a second end wherein the surgical tip comprises a cutting or ablating surface comprising a ferromagnetic material coating and in electrically conductive communication with a surface of an elongate section of the continuous conductor to form a ferromagnetic region between the first end and the second end; the first end or the second end of the continuous conductor having a conductivity and configured such that passage of electrical energy from a conductor location prior to the ferromagnetic region to a conductor location beyond the ferromagnetic region causes the ferromagnetic material to heat; and
wherein the ferromagnetic material has a thickness of between about 1 μm and about 50 μm.

21. The surgical tip of claim 20, wherein the continuous conductor forms a loop defining a void.

22. The surgical tip of claim 20, wherein the continuous conductor comprises a material having a Young's Modulus of about 400 GPa so that the continuous conductor resists bending when used to treat tissue.

23. The surgical tip claim 20, wherein the continuous conductor comprises tungsten.

24. The surgical tip of claim 20, wherein the continuous conductor has at least one intervening layer disposed between the continuous conductor and the ferromagnetic material.

25. The surgical tip of claim 20, wherein the ferromagnetic material is disposed circumferentially around the continuous conductor.

26. The surgical tip of claim 20, wherein the heatable ferromagnetic region is adapted to simultaneously resect tissue while causing hemostasis.

27. The surgical tip of claim 20, wherein the ferromagnetic material has a thickness of between about 2 μm and about 30 μm.

28. The surgical tip of claim 20, wherein the ferromagnetic material has a thickness of between about 2 μm and about 10 μm.

29. The surgical tip of claim 20, wherein the ferromagnetic material has a thickness sufficient to prevent fracturing of the ferromagnetic material when subjected to thermal stress passing from a first medium to a second medium.

* * * * *